US005863930A

United States Patent [19]

Dressel et al.

[11] Patent Number: 5,863,930

[45] **Date of Patent: *Jan. 26, 1999**

[54] TRISUBSTITUTED BIPHENYLS

[75] Inventors: Jürgen Dressel; Peter Fey, both of Wuppertal; Rudolf Hanko, Düsseldorf; Walter Hübsch, Wuppertal; Thomas Kramer, Wuppertal; Ulrich E. Müller, Wuppertal; Matthias Müller-Gliemann, Solingen-Ohligs; Martin Beuck, Erkrath; Stanislav Kazda, Wuppertal; Stefan Wohlfeil, Hilden; Andreas Knorr, Erkrath; Johannes-Peter Stasch, Solingen; Siegfried Zaiss, Wuppertal, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 574,082

[22] Filed: Dec. 18, 1995

Related U.S. Application Data

[62] Division of Ser. No. 368,252, Jan. 3, 1995, Pat. No. 5,596, 006, which is a continuation of Ser. No. 137,661, Oct. 15, 1993, abandoned.

[30] Foreign Application Priority Data

| | | | |
|---|---|---|---|
| Oct. 23, 1992 | [DE] | Germany | 42 35 933.3 |
| Jun. 8, 1993 | [DE] | Germany | 43 19 041.3 |

[51] Int. Cl.$^6$ .......................... A61K 31/44; C07D 401/10

[52] U.S. Cl. .......................... 514/340; 546/268.4; 546/298

[58] Field of Search .................................... 514/340, 350; 546/268.4, 298

[56] References Cited

U.S. PATENT DOCUMENTS

| | | | |
|---|---|---|---|
| 4,946,841 | 8/1990 | Baader et al. | 544/244 |
| 5,130,318 | 7/1992 | Roberts et al. | 546/153 |
| 5,130,439 | 7/1992 | Lo et al. | 548/110 |
| 5,206,374 | 4/1993 | Lo | 548/110 |
| 5,250,548 | 10/1993 | Winn et al. | 546/268.4 |
| 5,256,202 | 10/1993 | Hanamura et al. | 148/421 |
| 5,310,928 | 5/1994 | Lo et al. | 548/252 |
| 5,399,566 | 3/1995 | Katano et al. | 514/340 |

FOREIGN PATENT DOCUMENTS

| | | |
|---|---|---|
| 2051705 | 12/1991 | Canada . |
| 0399731 | 11/1990 | European Pat. Off. . |
| 0399732 | 11/1990 | European Pat. Off. . |
| 0403158 | 12/1990 | European Pat. Off. . |
| 0403159 | 12/1990 | European Pat. Off. . |
| 0407102 | 1/1991 | European Pat. Off. . |
| 0425211 | 5/1991 | European Pat. Off. . |
| 0487745 | 6/1992 | European Pat. Off. . |
| 0500297 | 8/1992 | European Pat. Off. . |
| 0542059 | 5/1993 | European Pat. Off. . |
| 9101001 | 1/1991 | WIPO . |
| 9310106 | 5/1993 | WIPO . |

OTHER PUBLICATIONS

Russell Ross, "The Smooth Muscle Cell", *The Journal of Cell Biology,* vol. 50, 1971, pp. 172–186.

Journal of Hypertension 1991, 9:3–15, Angiotensin and cell growth: a link to cardiovascular hypertrophy.

Young S. Lo et al., *J. Org. Chem.,* vol. 59, pp. 6391–6394 (1994).

*Primary Examiner*—Jane Fan
*Attorney, Agent, or Firm*—Sprung Kramer Schaefer & Briscoe

[57] ABSTRACT

Trisubstituted biphenyls are prepared by reacting corresponding pyridones with biphenylmethyl halogen compounds. The trisubstituted biphenyls can be employed as active compounds in medicaments.

15 Claims, No Drawings

TRISUBSTITUTED BIPHENYLS

This application is a divisional of application Ser. No. 08/368,252, filed Jan. 3, 1995, now U.S. Pat. No. 5,596,006 issued Jan. 21, 1997, which is a continuation of application Ser. No. 08/137,661, filed Oct. 15, 1993, now abandoned.

The invention relates to trisubstituted biphenyls, processes for their preparation and their use in medicaments, in particular as antihypertensive and antiatherosclerotic agents.

It is known that renin, a proteolytic enzyme, splits off the decapeptide angiotensin I from angiotensinogen in vivo, the angiotensin I in turn being broken down in the lung, kidneys or other tissues to give the hypertensive octapeptide angiotensin II. The various effects of angiotensin II, such as, for example, vasoconstriction, $Na^+$ retention in the kidneys, release of aldosterone in the adrenals and an increase in the tonicity of the sympathetic nervous system, have a synergistic action in the context of increasing blood pressure.

Angiotensin II moreover has the property of promoting the growth and multiplication of cells, such as, for example, of cardiac muscle cells and smooth muscle cells, these growing and proliferating to an increased degree under various disease states (for example hypertension, atherosclerosis and cardiac insufficiency).

In addition to inhibition of renin activity, a possible starting point for intervention in the renin-angiotensin system (RAS) is inhibition of the activity of angiotensin-converting enzyme (ACE) and blockade of angiotensin II receptors.

Pyridone-substituted biphenyls having antihypertensive properties are described in European Patent Applications EP 487 745 and 500 297.

The invention thus relates to a selection of trisubstituted biphenyls of the general formula (I)

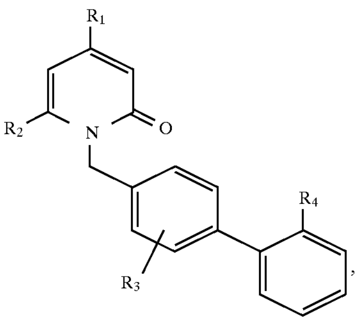

(I)

in which $R_1$ represents a carboxyl radical or represents a $C_1$–$C_8$-alkoxycarbonyl radical, $R_2$ represents straight-chain or branched $C_1$–$C_8$-alkyl, $R_3$ represents halogen, cyano, hydroxyl, $C_1$–$C_8$-alkoxy, straight-chain or branched $C_1$–$C_9$-alkyl, trifluoromethyl, trifluoromethoxy, carboxamido, carboxyl, $C_1$–$C_8$-alkoxycarbonyl or nitro and $R_4$ represents a carboxyl radical or represents tetrazolyl, and salts thereof.

The trisubstituted biphenyls according to the invention can also be in the form of their salts. Salts with organic or inorganic bases may be mentioned in general here.

Physiologically acceptable salts are preferred in the context of the present invention.

Physiologically acceptable salts of the trisubstituted biphenyls are in general metal or ammonium salts of the compounds according to the invention. Particularly preferred salts are, for example, lithium, sodium, potassium, magnesium or calcium salts, as well as ammonium salts which are derived from ammonia or organic amines, such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms either as enantiomers or as diastereomers. The invention relates both to the enantiomers or diastereomers and to their particular mixtures. The racemate forms can be separated into the stereoisomerically uniform constituents in a known manner, as can the diastereomers [cf. E. L. Eliel, Stereochemistry of Carbon Compounds, McGraw Hill, 1962]. The formation of atropic isomers is also possible.

Preferred compounds of the general formula (I) are those in which $R_1$ represents a carboxyl radical or represents a $C_1$–$C_6$-alkoxycarbonyl radical, $R_2$ represents straight-chain or branched $C_1$–$C_6$-alkyl, $R_3$ represents fluorine, chlorine, bromine, cyano, hydroxyl, $C_1$–$C_4$-alkoxy, straight-chain or branched $C_1$–$C_6$-alkyl, trifluoromethyl, trifluoromethoxy, carboxamido, carboxyl, $C_1$–$C_6$-alkoxycarbonyl or nitro and $R_4$ represents tetrazolyl, and salts thereof.

Particularly preferred compounds of the general formula (I) are those in which $R_1$ represents a carboxyl radical or represents a $C_1$–$C_4$-alkoxycarbonyl radical, $R_2$ represents straight-chain or branched $C_1$–$C_5$-alkyl, $R_3$ represents fluorine, chlorine, cyano, hydroxyl, $C_1$–$C_3$-alkoxy, straight-chain or branched $C_1$–$C_4$-alkyl, trifluoromethyl, trifluoromethoxy, carboxamido, carboxyl, $C_1$–$C_4$-alkoxycarbonyl or nitro and $R_4$ represents tetrazolyl, and salts thereof.

Especially preferred compounds of the general formula (I) are those in which $R_1$ represents carboxyl, methoxycarbonyl or ethoxycarbonyl, $R_2$ represents propyl, butyl or pentyl, $R_3$ represents fluorine, chlorine, cyano, hydroxyl, methyl, ethyl, methoxy, ethoxy, trifluoromethyl, trifluoromethoxy, carboxamido, carboxyl, methoxycarbonyl, ethoxycarbonyl or nitro, and $R_4$ represents tetrazolyl, and salts thereof.

The trisubstituted biphenyls of the general formula (I) are prepared by a process in which

[A] pyridones of the general formula (II)

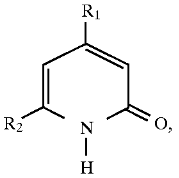

(II)

in which $R_1$ and $R_2$ have the abovementioned meaning, are reacted with compounds of the general formula (III)

(III)

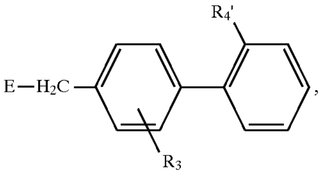

in which $R_3$ has the abovementioned meaning, $R_4$ represents $C_1$–$C_6$-alkoxycarbonyl or represents a radical of the formula

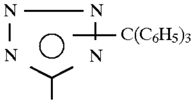

and

E represents chlorine or bromine, in inert solvents, in the presence of a base and if appropriate with addition of a catalyst, or

[B] in the case where $R^4$ represents tetrazolyl, compounds of the general formula (IV)

(IV)

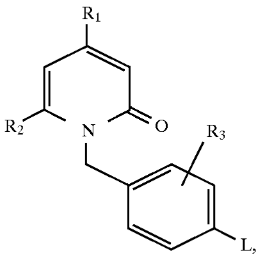

in which $R_1$, $R_2$ and $R_3$ have the abovementioned meaning and

L represents a typical leaving group, such as, for example, bromine, iodine or methane-, toluene-, fluorine- or trifluoromethanesulphonyloxy, preferably bromine, are reacted with compounds of the general formula (V)

(V)

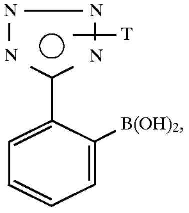

in which

T represents hydrogen, or represents the triphenylmethyl group, in inert solvents, in the presence of a base and under metal catalysis, and subsequently, in the case of the free tetrazole ($R_4$/T) the triphenylmethyl group is split off with acids in organic solvents and/or water, and in the case of the carboxylic acids ($R^4$/$R^1$), the corresponding ester is hydrolysed, and if appropriate the compounds are converted into their salts using bases.

The process according to the invention can be illustrated by way of example by the following equation:

[A]

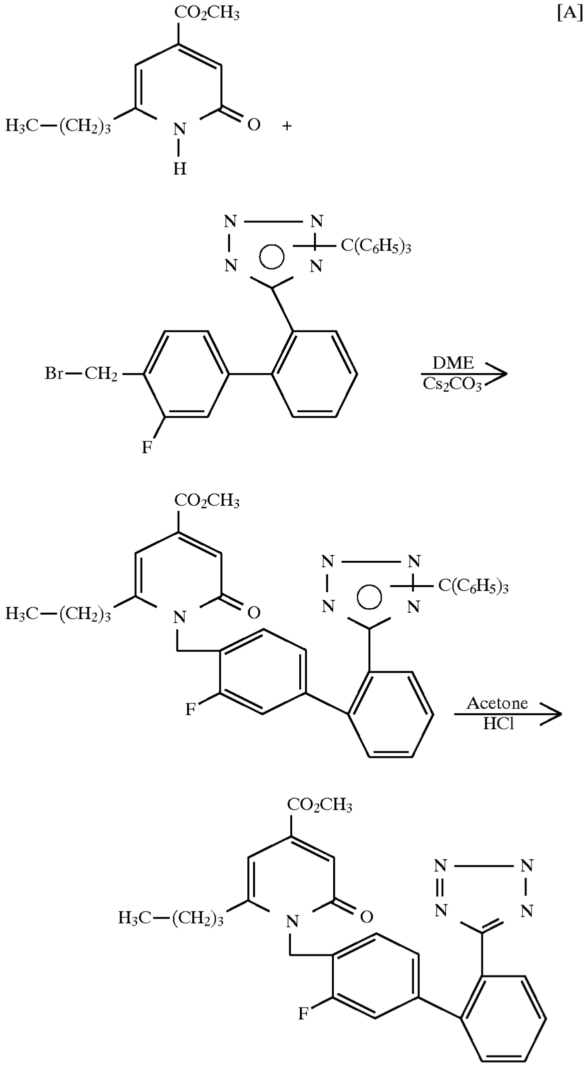

[B]

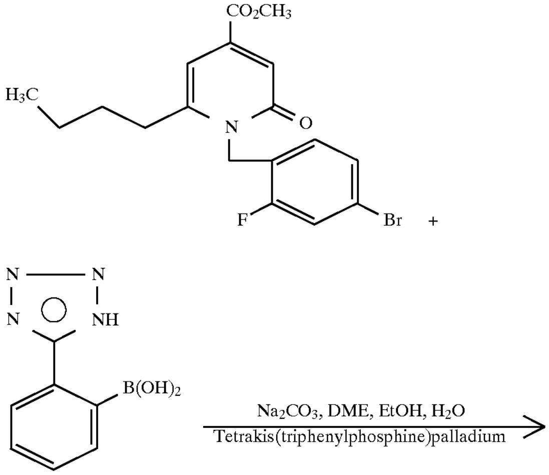

-continued

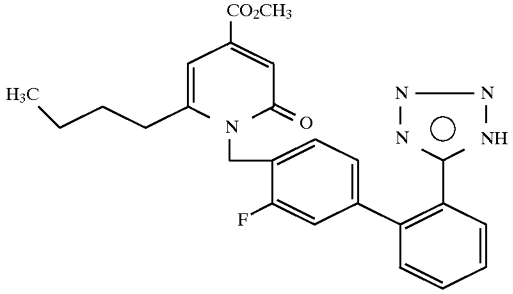

Suitable solvents for process [A] are the customary organic solvents which do not change under the reaction conditions. These include, preferably, ethers, such as diethyl ether, dioxane, tetrahydrofuran or dimethoxyethane, or hydrocarbons, such as benzene, toluene, xylene, hexane, cyclohexane or petroleum fractions, or halogenohydrocarbons, such as methylene chloride, chloroform, carbon tetrachloride, dichloroethylene, trichloroethylene or chlorobenzene, or ethyl acetate, dimethyl sulphoxide, dimethylformamide, hexamethylphosphoric acid triamide, acetonitrile, acetone or nitromethane. It is likewise possible to use mixtures of the solvents mentioned. Tetrahydrofuran, acetone, dimethylformamide and dimethoxyethane are preferred.

Inorganic or organic bases can in general be employed as bases for the process according to the invention. These bases include, preferably, alkali metal hydroxides, such as, for example, lithium hydroxide, sodium hydroxide or potassium hydroxide, alkaline earth metal hydroxides, such as, for example, barium hydroxide, alkali metal carbonates, such as sodium carbonate or potassium carbonate, alkali metal or alkaline earth metal carbonates, such as calcium carbonate or caesium carbonate, or alkali metal or alkaline earth metal alcoholates or amides, such as sodium methanolate or potassium methanolate, sodium ethanolate or potassium ethanolate or potassium tertbutylate, or lithium diisopropylamide (LDA), or organic amines (trialkyl($C_1$–$C_6$)amines), such as triethylamine, or heterocyclic compounds, such as 1,4-diazabicyclo[2.2.2]octane (DABCO), 1,8-diazabicyclo [5.4.0]undec-7-ene (DBU), pyridine, diaminopyridine, methylpiperidine or morpholine. It is also possible to employ alkali metals, such as sodium, or hydrides thereof, such as sodium hydride, as bases. Potassium carbonate, sodium hydride, potassium tert-butylate or caesium carbonate are preferred.

The base in case [A] is in general employed in an amount of 0.05 mol to 10 mol, preferably 1 to 2 mol, per mol of the compound of the formula (III).

Process [A] according to the invention is in general carried out in a temperature range from −100° C. to +100° C., preferably from 0° C. to 80° C.

The processes according to the invention are in general carried out under normal pressure. However, it is also possible to carry out the processes under increased pressure or under reduced pressure (for example in a range from 0.5 to 5 bar).

Suitable solvents for process [B] according to the invention are the customary organic solvents which do not change under the reaction conditions. These include, preferably, ethers, such as diethyl ether, dioxane, tetrahydrofuran or dimethoxyethane, or hydrocarbons, such as benzene, toluene, xylene, hexane, cyclohexane or petroleum fractions, or halogenohydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is also possible to use mixtures of the solvents mentioned. Tetrahydrofuran, acetone, dimethylformamide and dimethoxyethane are preferred. It is likewise possible to use mixtures of the solvents mentioned with water.

Process [B] according to the invention is in general carried out in a temperature range from −20° C. to +150° C., preferably from +40° C. to +100° C.

Suitable catalysts are in general metal complexes of nickel, palladium or platinum, preferably palladium(0) complexes, such as, for example, tetrakistriphenylphosphinepalladium. It is also possible to employ phase transfer catalysts, such as, for example, tetra-n-butylammonium bromide or crown ethers.

The catalyst is employed in an amount of 0.005 mol to 0.2 mol, preferably 0.01 mol to 0.05 mol, per mol of the compound of the general formula (IV).

Suitable bases are in general organic tertiary, non-nucleophilic bases, such as, for example, triethylamine or diisopropylethylamine, or inorganic bases, such as alkali metal carbonates or hydroxides, for example potassium carbonate or hydroxide, sodium carbonate or hydroxide or thallium carbonate or hydroxide, or alkoxides of these alkali metals. Sodium carbonate or potassium carbonate are preferred.

The base is in general employed in an amount of 1 mol to 10 mol, preferably 1 mol to 5 mol, in each case per mol of the compounds of the formula (IV).

If appropriate, the inorganic bases are employed in aqueous solution.

The triphenylmethyl group is split off with acetic acid or trifluoroacetic acid and water or one of the abovementioned alcohols, or with aqueous hydrochloric acid in the presence of acetone, or likewise with alcohols, or with a solution of hydrogen chloride in dioxane.

The splitting off is in general carried out in a temperature range from 0° C. to 150° C., preferably from 20° C. to 100° C., under normal pressure.

Suitable catalysts are potassium iodide or sodium iodide, preferably sodium iodide.

Suitable bases for the hydrolysis of the esters are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate, or alkali metal alcoholates, such as sodium methanolate, sodium ethanolate, potassium methanolate, potassium ethanolate or potassium tert-butanolate. Sodium hydroxide or potassium hydroxide are particularly preferably employed.

Suitable solvents for the hydrolysis are water or the organic solvents customary for hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

If appropriate, the hydrolysis can also be carried out with acids, such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mol of the ester. Molar amounts of the reactants are particularly preferably used.

The hydrolysis of tert-butyl esters is in general carried out with acids, such as, for example, hydrochloric acid or trifluoroacetic acid, in the presence of one of the abovementioned solvents and/or water or mixtures thereof, preferably with dioxane or tetrahydrofuran.

The compounds of the general formula (II) are known in some cases and can be prepared by known methods.

The compounds of the general formula (III) are known in some cases or can be prepared by known methods.

The compound of the formula (V) in the case where (T═H) is new and can be prepared by a process in which phenyltetrazole is first reacted in an inert solvent and in the presence of a base under an inert gas atmosphere, trimethyl borate is then added and the product is hydrolysed with acids in a last step.

Suitable solvents for the process are aprotic solvents, such as ethers, for example tetrahydrofuran, diethyl ether, toluene, hexane or benzene. Tetrahydrofuran is preferred.

Suitable bases are prim-, sec- and tert-butyllithium and phenyllithium. n-Butyllithium is preferred.

The base is employed in an amount of 2 mol to 5 mol, preferably 2 mol to 3 mol, per mol of phenyltetrazole.

Suitable acids are in general mineral acids, such as, for example, hydrochloric acid, $C_1$–$C_4$-carboxylic acids, such as, for example, acetic acid, or phosphoric acids. Hydrochloric acid is preferred.

The acid is in general employed in an amount of 1 mol to 10 mol, preferably 1 mol to 3 mol.

The process is in general carried out in a temperature range from −70° C. to +25° C., preferably −10° C. to 0° C.

The process according to the invention is in general carried out under normal pressure. However, it is also possible to carry out the process under increased pressure or under reduced pressure (for example in a range from 0.5 to 5 bar).

The compounds of the general formula (IV) are new in most cases and can be prepared, for example, by a process in which compounds of the general formula (VI)

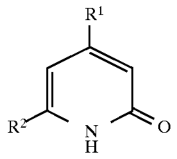

(VI)

in which $R^1$ and $R^2$ have the abovementioned meaning, are reacted with compounds of the general formula (VII)

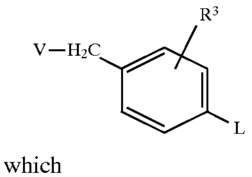

(VII)

in which $R^3$ and L have the abovementioned meaning and

V represents halogen, preferably bromine, in inert solvents, in the presence of a base and/or catalyst.

Suitable solvents for the process are customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as methylene chloride, chloroform, carbon tetrachloride, dichloroethylene, trichloroethylene or chlorobenzene, or ethyl acetate, dimethyl sulphoxide, dimethylformamide or dimethoxyethane, hexamethylphosphoric acid triamide, acetonitrile, acetone or nitromethane. It is also possible to use mixtures of the solvents mentioned. Tetrahydrofuran, acetone, dimethylformamide, dimethoxyethane, alcohols, such as methanol, ethanol or propanol, and/or water, toluene and methanol/water are preferred for the process.

Bases which can be employed for the processes according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate or caesium carbonate, or alkali metal or alkaline earth metal alcoholates or amides, such as sodium methanolate or potassium methanolate, sodium or potassium ethanolate or potassium tert-butylate, thallium carbonate or hydroxide, or lithium diisopropylamide (LDA), or organic amines (trialkyl($C_1$–$C_6$)amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, or hydrides thereof, such as sodium hydride, as bases. Potassium carbonate, sodium hydride, potassium tert-butylate or sodium carbonate are preferred for the process.

The base is in general employed in an amount of 0.05 mol to 10 mol, preferably 1 mol to 2 mol, in each case per mol of the compounds of the formula (VII).

The process according to the invention is in general carried out in a temperature range from −100° C. to +100° C., preferably from 0° C. to 80° C., under an inert gas atmosphere.

The process according to the invention is in general carried out under normal pressure. However, it is also possible to carry out the process under increased pressure or under reduced pressure (for example in a range from 0.5 to 5 bar).

Suitable catalysts for the process are potassium iodide or sodium iodide, preferably sodium iodide. It is also possible to employ phase transfer catalysts, such as, for example, tetra-n-butylammonium bromide or crown ethers.

The catalyst is employed in an amount of 0.1 mol to 10 mol, preferably 1 mol to 2 mol, per mol of the compound of the general formula (VII).

The above preparation processes are given merely for illustration. The preparation of the compounds of the general formula (I) according to the invention is not limited to these processes, and any modification of these processes can be used for the preparation in the same manner.

The trisubstituted biphenyls according to the invention exhibit an unforeseeable and valuable spectrum of pharmacological action.

The compounds according to the invention have a specific A II-antagonistic action, since they competitively inhibit bonding of angiotensin II to the receptors. They suppress the vasoconstrictory and aldosterone secretion-stimulating effects of angiotensin II. They moreover inhibit proliferation of smooth muscle cells.

They can therefore be employed in medicaments for the treatment of arterial hypertension and atherosclerosis. They can moreover be employed for the treatment of coronary heart diseases, cardiac insufficiency, disturbances in cerebral performance, ischaemic cerebral diseases, peripheral circulatory disturbances, dysfunctions of the kidneys and adrenals, bronchospastic and vascular-related diseases of the respiratory passages, sodium retention and oedemas.

Investigation of the Inhibition of Contractions Induced by Agonists

Rabbits of both sexes are stunned by a blow to the neck and exsanguinated, or in some cases anaesthetised with Nembutal (about 60–80 mg/kg intravenously) and sacrificed by opening the thorax. The thoracic aorta is removed, freed from adhering connective tissue, divided into ring segments 1.5 mm wide and introduced individually, under an initial load of about 3.5 g, in 10 ml organ baths containing carbogen-gassed Krebs-Henseleit nutrient solution, temperature-controlled at 37° C., of the following composition: 119 mmol/l of NaCl; 2.5 mmol/l of $CaCl_2 \times 2\ H_2O$; 1.2 mmol/l of $KH_2PO_4$; 10 mmol/l of glucose; 4.8 mmol/l of KCl; 1.4 mmol/l of $MgSO_4 \times 7\ H_2O$ and 25 mmol/l of $NaHCO_3$.

The contractions are recorded isometrically by Statham UC2 cells via bridge amplifiers (from Mülheim or DSM Aalen) and digitalised by means of an A/D converter (system 570, Keithley Munich) and evaluated. The agonist/dose effect curves (DEC) are plotted hourly. With each DEC, 3 or 4 individual concentrations are applied to the baths at intervals of 4 minutes. After the end of the DECs and subsequent wash-out cycles (16 times for in each case about 5 seconds/minutes with the abovementioned nutrient solution), a 28 minute rest or incubation phase follows, within which the contractions as a rule reach the starting value again.

The level of the 3rd DEC in the normal case is used as the reference parameter for evaluation of the test substance to be investigated in subsequent passes, the test substance being applied to the baths during the subsequent DECs in each case in an increasing dosage at the start of the incubation period. In this procedure, each aortic ring is always stimulated with the same agonist over the whole day.

Agonists and their standard concentrations (application volume per individual dose=100 μl):

| | | |
|---|---|---|
| KCl | 22.7; 32.7; 42.7; 52.7 | mmol/l |
| 1-noradrenaline | $3 \times 10^{-9}$; $3 \times 10^{-8}$; $3 \times 10^{-7}$; $3 \times 10^{-6}$ | g/ml |
| serotonin | $10^{-8}$; $10^{-6}$; $10^{-7}$; $10^{-5}$ | g/ml |
| B-HT 920 | $10^{-7}$; $10^{-6}$; $10^{-5}$ | g/ml |
| methoxamine | $10^{-7}$; $10^{-6}$; $10^{-5}$ | g/ml |
| angiotensin II | $3 \times 10^{-9}$; $10^{-8}$; $3 \times 10^{-8}$; $10^{-7}$ | g/ml |

To calculate the $IC_{50}$ (concentration at which the substance to be investigated causes 50% inhibition), the effect in each case at the 3rd=submaximum agonist concentration is taken as the basis.

The compounds according to the invention inhibit the angiotensin II-induced contraction of the isolated rabbit aorta as a function of the dose. The contraction induced by potassium depolarisation or other agonists was not inhibited or only weakly inhibited at high concentrations.

Blood Pressure Measurements on the Angiotensin II-infused Rat

Male Wistar rats (Moellegaard, Copenhagen, Denmark) having a body weight of 300–350 g are anaesthetised with thiopental (100 mg/kg intraperitoneally). After tracheotomy, a catheter for blood pressure measurement is introduced into the femoral artery and a catheter for angiotensin II infusion and a catheter for administration of the substance are introduced into the femoral veins. After administration of the ganglionic blocker pentolinium (5 mg/kg intravenously), the angiotensin II infusion (0.3 μg/kg/minute) is started. As soon as the blood pressure values have reached a stable plateau, the test substances are administered either intravenously, or orally as a suspension or solution in 0.5% Tylose. The changes in blood pressure under the influence of the substance are stated as mean values±SEM in the table.

Determination of the Antihypertensive Activity on Conscious Hypertensive Rats The oral antihypertensive activity of the compounds according to the invention was tested on conscious rats with surgically induced unilateral renal artery stenosis. For this, the right-hand renal artery was constricted with a silver clip of 0.18 mm internal diameter. With this form of hypertension, the plasma renin activity is increased in the first six weeks after the intervention. The arterial blood pressure of these animals was measured bloodlessly using a "tail cuff" at defined intervals of time after administration of the substance. The substances to be tested were administered intragastrally ("orally") by gavage in various doses as a suspension in a Tylose suspension. The compounds according to the invention lower the arterial blood pressure of the hypertensive rats in a clinically relevant dosage.

The compounds according to the invention moreover inhibit the specific bonding of radioactive angiotensin II as a function of their concentration.

Interaction of the Compound According to the Invention with Angiotensin II Receptor on Membrane Fractions of the Adrenal Cortex (Bovine)

Freshly removed bovine adrenal cortices (AC) thoroughly freed from the medulla of the capsule are comminuted in sucrose solution (0.32M) with the aid of an Ultra-Turrax (Janke & Kunkel, Staufen i.B.) to a coarse membrane homogenate and partly purified to membrane fractions in two centrifugation steps.

The studies on receptor bonding are carried out on partly purified membrane fractions of bovine AC with radioactive angiotensin II in an assay volume of 0.25 ml, which comprises, specifically, the partly purified membranes (50–80 μg), $^3$H-angiotensin II (3–5 nM), test buffer solution (50 mM Tris, pH 7.2), 5 mM $MgCl_2$ and the substances to be investigated. After an incubation time of 60 minutes at room temperature, the non-bonded radioactivity of the samples is separated off by means of moistened glass fibre filters (Whatman GF/C) and the radioactivity bonded is measured spectrophotometrically in a scintillation cocktail after the protein has been washed with ice-cold buffer solution (50 mM Tris/HCl, pH 7.4, 5% of PEG 6000). The raw data were analysed with computer programs to give $K_i$ and $IC_{50}$ values ($K_i$: $IC_{50}$ values corrected for the radioactivity used; $IC_{50}$ values: concentration at which the substance to be investigated causes 50% inhibition of specific bonding of the radioligands).

Investigation of the Inhibition of Proliferation of Smooth Muscle Cells by the Compounds According to the Invention Smooth muscle cells which have been isolated from the aortas of rats by the media explantate technique [R. Ross, J.

Cell. Biol. 50, 172, 1971] are used to determine the antiproliferative action of the compounds. The cells are sown in suitable culture dishes, as a rule 96-well plates, and cultured at 37° C. for 2–3 days in medium 199 with 7.5% of FCS and 7.5% of NCS, 2 mM L-glutamine and 15 mM HEPES, pH 7.4, in 5% $CO_2$. Thereafter, the cells are synchronised by withdrawal of serum for 2–3 days and are then stimulated to growth with serum or other factors. Test compounds are added at the same time. 1 μCi $^3$H-thymidine is added after 16–20 hours, and the incorporation of this substance into the DNA of the cells which can be precipitated with TCA is determined after a further 4 hours.

The active compound concentration which causes half the maximum inhibition of thymidine incorporation caused by 10% of FCS on sequential dilution of the active compound is calculated for the determination of the $IC_{50}$ values.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents.

The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Administration is effected in the customary manner, preferably orally or parenterally, in particular perlingually or intravenously.

In the case of parenteral use, solutions of the active compound can be employed, using suitable liquid excipient materials.

In general, it has proved advantageous in the case of intravenous administration to administer amounts of about 0.001 to 1 mg/kg, preferably about 0.01 to 0.5 mg/kg of body weight to achieve effective results, and in the case of oral administration, the dosage is about 0.01 to 20 mg/kg, preferably 0.1 to 10 mg/kg of body weight.

Nevertheless, it may at times be necessary to deviate from the dosages mentioned, and in particular to do so as a function of the body weight or the nature of the administration route, or of the behaviour of the individual towards the medicament, of the nature of its formulation and of the time or interval at which administration takes place. Thus, in some cases it may be sufficient to employ less than the abovementioned minimum amount, while in other cases the upper limit mentioned must be exceeded. If relatively large amounts are administered, it may be advisable to divide these into several individual doses over the course of the day.

Starting Compounds

EXAMPLE I

N-(1-Hydroxy-2-methyl-prop-2-yl)-2-methoxy-benzoic acid amide

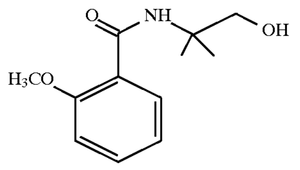

15.2 g (100 mmol) of 2-methoxy-benzoic acid are dissolved in 300 ml of methylene chloride and the solution is stirred with 14.2 g (105 mmol) of 1-hydroxy-benzoic acid triazole×1 $H_2O$ and 21.66 g (105 mmol) of N,N-dicyclohexylcarbodiimide at 0° C. The suspension thus obtained is stirred at room temperature for 0.5 hour, cooled to 0° C. again, and a solution of 9.89 g (111 mmol) of 1-hydroxy-2-methyl-2-propylamine and 12.65 g (125 mmol) of triethylamine in 300 ml of methylene chloride is added. The reaction is complete after 1 hour. The reaction mixture is washed with 1M of hydrochloric acid and saturated sodium bicarbonate solution, dried over sodium sulphate and concentrated in vacuo. The crude product is stirred with petroleum ether, filtered off with suction, subsequently rinsed with the solvent and dried under a high vacuum.

EXAMPLE II 4,5-Dihydro-5,5-dimethyl-2-(2-methoxyphenyl)-oxazole

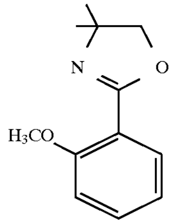

17.1 ml (283.4 mmol) of thionyl chloride are added to 16.0 g (71.7 mmol) of the compound from Example 1 at room temperature and stirred for 3 hours. Thereafter, excess reagent is evaporated off and the residue is extracted by stirring with 500 ml of ether and filtered off with suction. The solid is dissolved in water, the solution is covered with a layer of ether and the corresponding base is liberated with 2M sodium hydroxide solution. After the aqueous phase has been extracted three times with ethyl acetate, the combined organic phases are dried with sodium sulphate and evaporated and the residue is freed from the residual solvent under a high vacuum.

EXAMPLE III 4,5-Dihydro-5,5-dimethyl-2-(3'-fluoro-4'-methyl-biphenyl-2-yl)oxazole

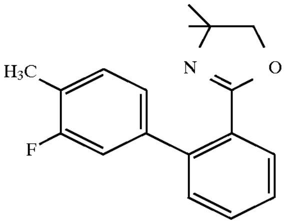

14.7 g (605.7 mol) of magnesium filings are initially introduced into 50 ml of analytical grade tetrahydrofuran under argon, and 117.7 g (623 mmol) of 4-bromo-2-fluoro-toluene in 500 ml of analytical grade tetrahydrofuran are added, while stirring. A clear solution forms at 35°–40° C. within 2 hours. A solution of 74.0 g (360.5 mmol) of the compound from Example II in 500 ml of analytical grade tetrahydrofuran is added dropwise at room temperature and the mixture is subsequently stirred at about 25° C. for 16 hours, initially with gentle cooling. The solvent is evaporated off and the crude product is subsequently rinsed in 600 ml of ethyl acetate and 800 ml of saturated ammonium chloride solution at 10° C., dried with sodium sulphate and evaporated in vacuo. For purification, the product is taken up in 600 ml of ether, any solid residue is filtered off with suction and the crude product is extracted into the aqueous phase by several extractions with 2M hydrochloric acid. This aqueous phase is covered with a layer of ether and brought to pH 13 with sodium hydroxide solution. After three extractions with ether, the product phase is dried with sodium sulphate and evaporated and the residual solvent is removed under a high vacuum.

EXAMPLE IV 2-(3-Fluoro-4-methylphenyl)-benzonitrile

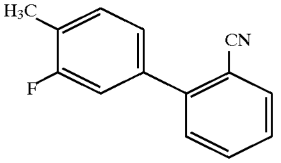

97.0 g (343 mmol) of the compound from Example III are initially introduced into 500 ml of pyridine, and 31.3 ml (343 mmol) of phosphorus oxychloride are added at 0° C., while stirring. The mixture is heated slowly, and is finally boiled under reflux for 1 hour. After cooling to room temperature, ether and an amount of 1M hydrochloric acid such that the pH of the aqueous phase is 1.5 are added. The organic phase is washed three more times with 1M sulphuric acid, dried with sodium sulphate and evaporated on a rotary evaporator and the residue is freed from the residual solvent under a high vacuum.

EXAMPLE V 5-(3'-Fluoro-4'-methyl-biphenyl-2-yl)-1H-tetrazole

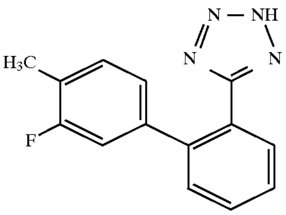

2.26 g (10.7 mmol) of the compound from Example IV are boiled under reflux with 3.48 g (53.6 mmol) of sodium azide and 7.37 g (53.6 mmol) of triethylammonium chloride in 30 ml of analytical grade dimethylformamide for 24 hours. After cooling, the mixture is partitioned between ether and 1M sulphuric acid, the organic phase is washed with water and dried over sodium sulphate and the solvent is evaporated off. The crude product is extracted by stirring in toluene and, after filtration with suction, the product is dried in vacuo (1.89 g, 7.2 mmol). The mother liquor is evaporated on a rotary evaporator and the residue is purified again as above (0.43 g, 1.7 mmol).

EXAMPLE VI 5-(3-Fluoro-4-methyl-biphenyl-2-yl)-N-triphenylmethyl-1H-tetrazole

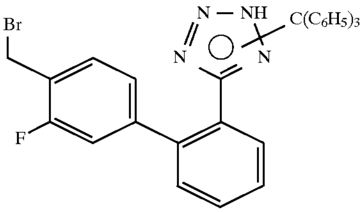

50.55 g (199.2 mmol) of the compound from Example V are stirred with 58.58 g (210.0 mmol) of triphenylchloromethane and 33.2 ml (239.0 mmol) of triethylamine in 700 ml of methylene chloride at room temperature for 17 hours. The reaction mixture is washed once with water and once with 1M aqueous citric acid, dried with sodium sulphate and evaporated on a rotary evaporator and the residue is freed from the residual solvent under a high vacuum.

EXAMPLE VII cl 5-(4'-Bromomethyl-3'-fluoro-biphenyl-2-yl)-N-triphenylmethyl-1H-tetrazole

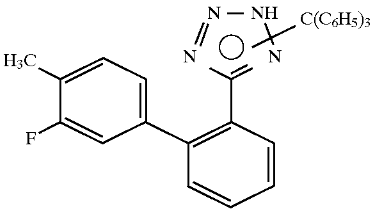

82.90 g (173.2 mmol) of the compound from Example VI are boiled under reflux with 30.84 g (173.2 mmol) of N-bromosuccinimide and 0.87 g (5.3 mmol) of azobisisobutyronitrile, as a free radical initiator, in 1 l of carbon tetrachloride for 6 hours. After cooling, the succinimide which has precipitated is filtered off with suction and washed with carbon tetrachloride. The filtrate is evaporated and the residue is dried under a high vacuum.

EXAMPLE VIII

6-Butyl-4-methoxycarbonyl-2-oxo-1,2-dihydropyridine

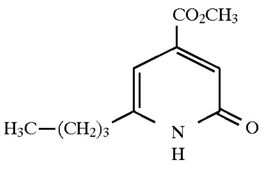

12.5 ml (0.17 mol) of thionyl chloride are added dropwise to a suspension of 29.25 g (0.15 mol) of 6-butyl-2-oxo-1,2-dihydro-isonicotinic acid in 200 ml of methanol, while cooling with ice, and the mixture is stirred overnight at room temperature. It is concentrated to dryness and the residue is chromatographed over 450 g of silica gel (230–400 mesh) using methylene chloride→methylene chloride/methanol 10:1. Colourless crystals of melting point 106° C. crystallise from methylene chloride, ether and petroleum ether.

EXAMPLE IX

6-Butyl-4-methoxycarbonyl-2-oxo-1-{[3-fluoro-2'-(N-triphenylmethyl-tetrazol-5-yl)-biphenyl-4-yl]methyl}-1,2-dihydropyridine

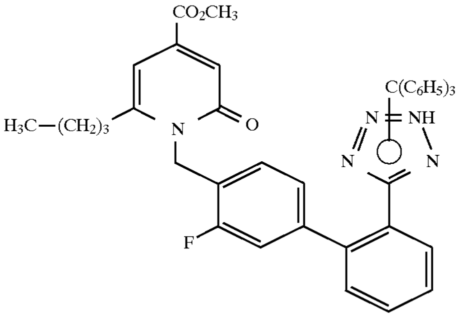

61.1 g (0.188 mol) of caesium carbonate are added to a solution of 31.4 g (0.15 mol) of the compound from Example VIII in 600 ml of dimethoxyethane, the mixture is stirred at room temperature for 15 minutes, 104 g (0.18 mol) of the compound from Example VII are then added, and the mixture is stirred at room temperature overnight and boiled under reflux for 3 hours. The reaction mixture is then partitioned between water and ethyl acetate (in each case 800 ml) and the organic phase is washed with saturated sodium chloride solution, dried over $Na_2SO_4$ and concentrated. The residue is filtered over 2 kg of silica gel (230–400 mesh) using petroleum ether/ethyl acetate (5:1)→(1:1).

EXAMPLE X 2-(Tetrazol-5'-yl)phenylboronic acid

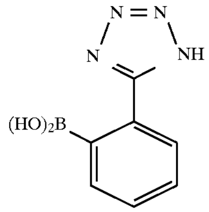

17.6 ml (44 mmol) of a 2.5M solution of n-butyllithium in n-hexane are added to a solution of 2.9 g (20 mmol) of 5-phenyltetrazole in 50 ml of tetrahydrofuran at −5° C. under argon. The mixture is stirred at −5° C. to 0C. for 30 minutes, and 10 ml (88 mmol) of boric acid trimethyl ester are added at this temperature. The cooling bath is then removed and 10 ml of half-concentrated hydrochloric acid are added to the solution at room temperature. After 1 hour, the mixture is extracted with 100 ml of ethyl acetate, the organic phase is separated off and the aqueous phase is extracted twice with 20 ml of ethyl acetate each time. The combined organic phases are dried over sodium sulphate and concentrated and the residue is purified on silica gel using toluene/glacial acetic acid/methanol (38:0.1:2).

Yield: 2.65 g (70% of theory)

$R_f$=0.26 (toluene/methanol/glacial acetic acid=32:8:1)

$^{13}$C-NMR: δ=156.7; 137.9; 133.5; 129.8; 128.9; 127.7; 126.9 ppm.

EXAMPLE XI

4-Bromo-3-methylbenzyl alcohol

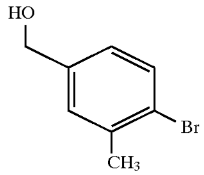

93 ml of a 1M solution of borane-tetrahydrofuran complex in tetrahydrofuran are added dropwise to a solution of 10 g (46.5 mmol) of 4-bromo-3-methyl-benzoic acid in 100 ml of tetrahydrofuran at 0° C. under argon. After the reaction mixture has been heated to 20° C., it is stirred at this temperature for 16 hours. The excess borane complex is then destroyed by careful addition of water (end of the evolution of hydrogen), the mixture is extracted twice with in each case 250 ml of ethyl acetate and the combined organic phases are washed twice with in each case 100 ml of saturated sodium bicarbonate solution, water and saturated sodium chloride solution, dried over sodium sulphate and concentrated. The compound is reacted further without purification.

Yield: 8 g (crude, 86% of theory)

$R_f$: 0.5 (petroleum ether/ethyl acetate=2:1)

EXAMPLE XII

4-Bromo-2-methylbenzyl alcohol

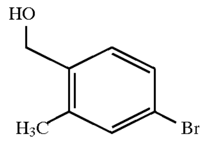

The title compound is obtained from 10 g (46.5 mmol) of 4-bromo-2-methylbenzoic acid analogously to the instructions of Example XI.

Yield: 10 g (crude, 107% of theory)

$R_f$: 0.73 (petroleum ether/ethyl acetate=2:1)

EXAMPLE XIII

4-Bromo-3-methylbenzyl bromide

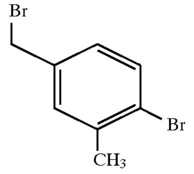

The title compound is obtained from 8 g (39.8 mmol) of the compound from Example XI analogously to the instructions of Example XLIX.

Yield: 6.4 g (61% of theory)

$R_f$: 0.75 (petroleum ether/ethyl acetate=10:1)

EXAMPLE XIV

4-Bromo-2-methylbenzyl bromide

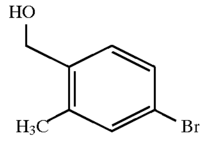

The title compound is obtained from 10 g (49.7 mmol) of the compound from Example XII analogously to the instructions of Example XLIX.

Yield: 10.9 g (83% of theory)

$R_f$: 0.8 (petroleum ether/ethyl acetate=10:1)

EXAMPLE XV

3-Amino-6-methylbenzonitrile

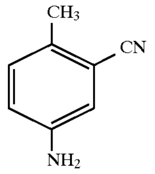

A suspension of 8.11 g (50 mmol) of 6-methyl-3-nitrobenzonitrile and 0.81 g of 10% of palladium-on-charcoal in 50 ml of ethanol and 50 ml of ethyl acetate is hydrogenated under 2.9 bar for 1 hour. The catalyst is filtered off, the filtrate is concentrated and the residue is crystallised from ether/petroleum ether.

Yield: 59.6% of theory

Melting point: 88° C.

EXAMPLE XVI

3-Bromo-6-methyl-benzonitrile

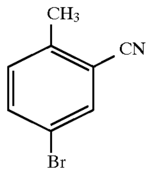

15.2 g (0.22 mol) of sodium nitrite are heated to 70° C. in 160 ml of concentrated sulphuric acid and the solution formed is added dropwise to a solution of 26.4 g (0.2 mol) of the compound from Example XV in 400 ml of glacial acetic acid at 20° C. to 40° C. A solution of 63.1 g (0.44 mol) of copper(I) bromide in 400 ml of concentrated hydrobromic acid is added dropwise to this solution at 10° C. to 20° C. and the mixture is stirred for 0.5 hour. The reaction mixture is introduced into 1 l of water, the precipitate which has separated out is filtered off with suction, washed with water and suspended in methylene chloride and the insoluble material is filtered off with suction. The filtrate is washed with saturated sodium chloride solution, dried over sodium sulphate and concentrated to give 19.2 g of the title compound.

Yield: 44.5% of theory $R_f$: 0.31 (petroleum ether/methylene chloride=1:2)

EXAMPLE XVII

3-Bromo-6-bromomethyl-benzonitrile

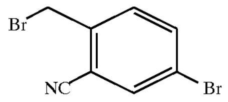

A suspension of 19.1 g (97.4 mmol) of the compound from Example XVI, 17.3 g (97.4 mmol) of N-bromosuccinimide and 0.2 g of azobisisobutyronitrile in 100 ml of carbon tetrachloride is stirred under reflux for 1 hour. The mixture is filtered, the filtrate is concentrated to dryness and the residue is crystallised from methanol to give 7.7 g of the title compound.

Yield: 28.7% of theory

Melting point: 81° C.

EXAMPLE XVIII

6-Butyl-4-methoxycarbonyl-2-oxo-1-(2-fluoro-4-iodophenylmethyl)-1,2-dihydropyridine

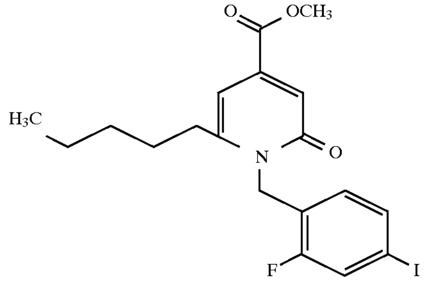

A solution of 2.09 g (10 mmol) of the compound from Example VIII, 3.14 g (10 mmol) of 2-fluoro-4-iodobenzyl bromide and 2.11 g (11 mmol) of caesium carbonate in 40 ml of DME is stirred at 20° C. under argon for 16 hours. The solvent is then removed in vacuo, the residue is taken up in methylene chloride/water, the aqueous phase is extracted once with methylene chloride and the combined organic phases are dried over sodium sulphate and concentrated. The residue is purified on silica gel using petroleum ether/ethyl acetate (5:1 and 3:1).

Yield: 1.1 g (25% of theory)

$R_f$: 0.44 (petroleum ether/ethyl acetate=3:1)

The compounds listed in Table I are prepared analogously to the instructions of Example XVIII:

TABLE I

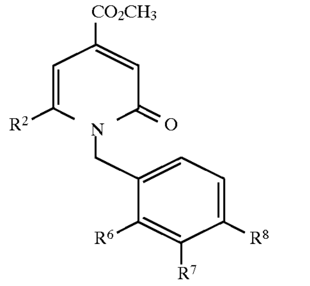

| Ex. No. | $R^2$ | $R^6$ | $R^7$ | $R^8$ | $R_f$(*) |
|---|---|---|---|---|---|
| XIX | $CH_3-(CH_2)_3-$ | $-F$ | H | $-Br$ | 0.34 (A) |
| XX | $CH_3-(CH_2)_3-$ | $-CH_3$ | H | Br | 0.44 (B) |
| XXI | $CH_3-(CH_2)_3-$ | H | $-CH_3$ | $-Br$ | 0.40 (A) |
| XXII | $CH_3-(CH_2)_4-$ | $-F$ | $-H$ | $-Br$ | 0.11 (C) |
| XXIII | $CH_3-(CH_2)_3-$ | $-Cl$ | $-H$ | $-I$ | 0.67 (D) |
| XXIV | $CH_3-(CH_2)_3-$ | H | F | Br | 0.27 (F) |
| XXV | $CH_3-(CH_2)_3-$ | CN | H | Br | 0.36 (F) |
| XXVI | $CH_3-(CH_2)_3-$ | H | Cl | Br | 0.38 (G) |
| XXVII | $CH_3(CH_2)_3-$ | H | Cl | I | 0.41 (G) |
| XXVIII | $CH_3(CH_2)_3-$ | $NO_2$ | H | Br | 0.22 (A) |
| XXIX | $CH_3(CH_2)_3-$ | H | $NO_2$ | Br | 0.46 (H) |
| XXX | $CH_3(CH_2)_3-$ | CN | H | Br | 0.40 (D) |

*Mobile phase mixtures:
A: petroleum ether:ethyl acetate 3:1
B: petroleum ether:ethyl acetate 2:1
C: petroleum ether:ethyl acetate 5:1
D: petroleum ether:ethyl acetate 1:1
E: petroleum ether:ethyl acetate 1:2
F: petroleum ether:ethyl acetate 2:1
G: hexane:ethyl acetate 1:1
H: methylene chloride:methanol 20:1

EXAMPLE XXXI

3-Chloro-4-iodo-toluene

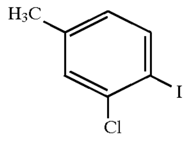

250 ml of concentrated hydrochloric acid and 75 g of 4-amino-3-chlorotoluene (0.53 mol) are introduced onto 166 g of ice, and a solution of 40.3 g of sodium nitrite (0.583 mol) in 170 ml of water is then added dropwise at 0° C. After the solution has been stirred for 15 minutes, it is filtered through glass wool, and the solution, which has been cooled to −2° C., is added dropwise to a solution, warmed to room temperature, of 455 g of potassium iodide (2.74 mol) in 1 l of water together with a batch prepared analogously with 0.30 mol of 4-amino-3-chloro-toluene. After the reaction mixture has been stirred overnight, it is extracted three times with ether and the combined organic phases are washed twice with dilute sodium hydroxide solution, twice with dilute sodium bisulphite solution and with water. After drying over sodium sulphate, filtration and concentration, the residue of copper powder is distilled over a Vigreux column under 1 mm Hg. The fraction between 70° and 85° C. gives 149 g of a yellow oil [7% of theory, $R_f$=0.57 (hexane:ethyl acetate=9:1)].

EXAMPLE XXXII

3-Chloro-4-iodo-benzyl bromide

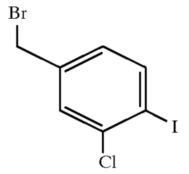

A suspension of 40.4 g (160 mmol) of the compound from Example XXXI in 400 ml of carbon tetrachloride, 31.3 g of N-bromosuccinimide (176 mmol) and 2.63 g of azobisisobutyronitrile (16 mmol) is heated under reflux overnight. After cooling, the precipitate is filtered off with suction and washed with carbon tetrachloride. The combined filtrates are concentrated and the residue is further reacted in the crude state.

EXAMPLE XXXIII

Methyl 3-chloro-4-trifluoromethylsulphonyloxy-benzoate

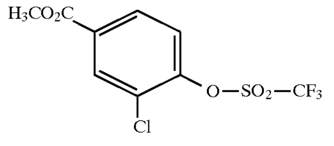

5.5 ml of trifluoromethanesulphonic anhydride (33 mmol) are slowly added dropwise to a solution of 5.49 g of methyl 3-chloro-4-hydroxy-benzoate (29.4 mmol) in 15 ml of pyridine at 0° C. After the reaction mixture has been stirred at 0° C. for 5 minutes and at room temperature for 4 hours, it is partitioned between water and ether. The organic phase is washed in succession with water, dilute hydrochloric acid, water and saturated sodium chloride solution, dried over sodium sulphate and concentrated and the residue is chromatographed over silica gel using methylene chloride to give 8.93 g of a pale yellow thinly mobile oil [95.2% of theory, $R_f$ 0.63 (hexane:ethyl acetate=3:1)].

EXAMPLE XXXIV 5-(2'-Chloro-4'-methoxycarbonyl-biphenyl-2-yl)-2-triphenylmethyl-1H-tetrazole

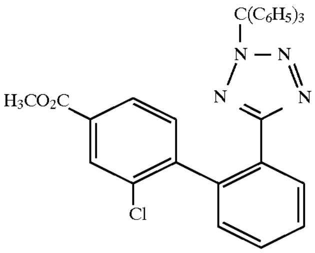

Argon is passed through a solution of 1.00 g (3.14 mmol) of the compound from Example XXXIII in 50 ml of toluene. After addition of 168 mg of Pd $(P(C_6H_5)_3)_4$ (0.146 mmol), 6 ml of methanol, 1.63 g (3.77 mmol) of 2-(N-triphenylmethyl-tetrazol-5-yl)-phenylboronic acid and a solution of 333 mg (3.14 mmol) of sodium carbonate in 4 ml of degassed water, the emulsion is stirred at 100° C. overnight. Addition of the same amount of catalyst, followed by stirring at 100° C. for 2.5 hours, brings the reaction to completion. The reaction mixture is partitioned between water and ethyl acetate, the organic phase is washed with dilute sodium carbonate solution and saturated sodium chloride solution, dried over sodium sulphate and concentrated and the residue is chromatographed over silica gel (hexane:ethyl acetate=10:1), to give 10.1 g of a pale yellow solid [57.9% of theory, $R_f$ 0.46 (hexane:ethyl acetate=3:1)].

EXAMPLE XXXV 5-(2'-Chloro-4'-hydroxymethyl-biphenyl-2-yl)-2-triphenyl-methyl-1H-tetrazole

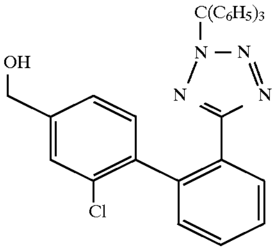

1.27 9 of methanol (39.6 mmol) and 1.29 g of lithium borohydride (59.4 mmol) are added to a solution of 22.0 g (39.6 mmol) of the compound from Example XXXIV in 180 ml of tetrahydrofuran, and the mixture is then stirred at room temperature for 30 minutes and under reflux for 1 hour. Addition of a further 0.63 g of methanol (0.20 mmol) and stirring under reflux for 1 hour brings the reaction to completion. The reaction mixture is concentrated; the residue is taken up in 200 ml of methylene chloride and 100 ml of 1N potassium hydrogen sulphate solution are slowly added under a vigorous stream of argon, using an ice-bath. After the phases have been separated, the aqueous phase is extracted with methylene chloride. The combined organic phases are washed with saturated sodium chloride solution, dried over sodium sulphate and concentrated, to give 20.5 g of white crystals [98.19% of theory; melting point 186°–7° C. (decomposition), $R_f$ 0.15 (hexane:ethyl acetate=3:1)].

EXAMPLE XXXVI 5-(4'-Bromomethyl-2'-chloro-biphenyl-2-yl)-2-triphenyl-methyl-1H-tetrazole

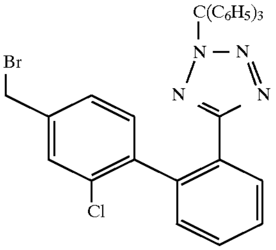

First 6.79 g of bromine (42.5 mmol) and then 20.4 g of the compound from Example XXXV in 300 ml of methylene chloride are added dropwise to a solution of 11.2 g of triphenylphosphine (42.5 mmol) in 100 ml of methylene chloride under argon in an ice-bath. After the reaction mixture has been stirred at room temperature for 1 hour, it is filtered through silica gel and eluted with methylene chloride. Concentration of the filtrate and digestion of the residue with hexane gives 15.8 g of white crystals [68.9% of theory; melting point 15°–60° C.; $R_f$ 0.40 (hexane/ethyl acetate=3:1)].

EXAMPLE XXXVII

2-Hydroxy-5-methoxycarbonyl-benzaldehyde oxime

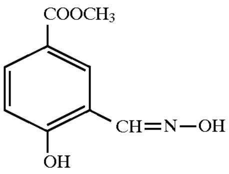

A solution of 68.0 g (0.83 mol) of sodium acetate and 68.0 g (0.98 mol) of hydroxylamine hydrochloride in 300 ml of water is added dropwise to a solution of 80.5 g (0.45 mol) of 2-hydroxy-5-methoxycarbonylbenzaldehyde in 300 ml of methanol and the mixture is stirred at 25° C. for 2 hours. The product which has precipitated is filtered off with suction, washed with water and dried in vacuo over phosphorus pentoxide to give 70.4 g of the title compound.

Yield: 80.7% of theory

Melting point: 155° C.

EXAMPLE XXXVIII

2-Acetoxy-5-methoxycarbonyl-benzonitrile

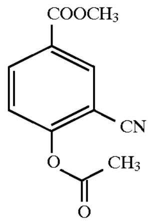

70.3 g (0.36 mol) of the compound from Example XXXVII are stirred under reflux in 0.5 l of acetic anhydride for 1.5 hours. The mixture is concentrated to dryness, the residue is dissolved in methylene chloride and the title compound is crystallised out by addition of petroleum ether.

Yield: 89.7% of theory

Melting point: 98° C.

EXAMPLE XXXIX

2-Hydroxy-5-methoxycarbonyl-benzonitrile

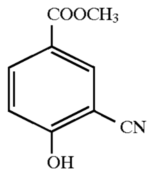

A suspension of 70.6 g (0.32 mol) of the compound from Example XXXVIII and 3.48 g (0.06 mol) of sodium methylate in 0.5 l of methanol is heated under reflux for 3 hours, the pH is brought to 6.5 with 1N hydrochloric acid at 25° C., the mixture is concentrated in vacuo, the residue is taken up in methylene chloride, the mixture is washed with saturated sodium chloride solution, the organic phase is dried over sodium sulphate and concentrated and the residue is crystallised from diethyl ether/petroleum ether mixtures.

Yield: 98% of theory

Melting point: 193°

EXAMPLE XL

Methyl 3-cyano-4-trifluoromethylsulphonyloxy-benzoate

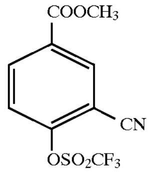

98.2 g of the title compound are obtained from 55.8 g (0.32 mol) of the compound of Example XXXIX analogously to the instructions of Example XXXIII.

Yield: 100% of theory $R_f$=0.63 (petroleum ether:ethyl acetate=2:1)

EXAMPLE XLI 5-(2'-Cyano-4'-methoxycarbonyl-biphenyl-2-yl)-2-triphenyl-1H-tetrazole

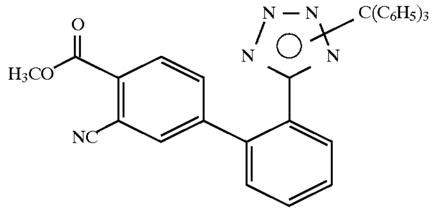

1.4 g of the title compound are obtained from 3.0 g (10 mmol) of the compound of Example XL analogously to the instructions of Example XXXIV.

Yield: 26.0% of theory

Melting point: 220°–240° C. (decomposition)

EXAMPLE XLII 5-(2'-Cyano-4'-hydroxymethyl-biphenyl-2-yl)-2-triphenylmethyl-1H-tetrazole

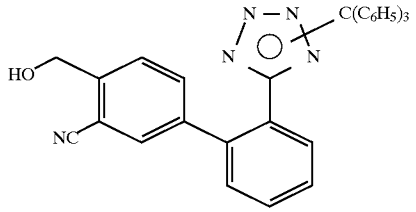

254 mg of the title compound are obtained from 410 mg of the compound of Example XLI analogously to the instructions of Example XXXV.

Yield: 64.4% of theory

Melting point: 208° C.

EXAMPLE XLIII 5-(4'-Bromomethyl-2'-cyano-biphenyl-2-yl)-2-triphenylmethyl-1H-tetrazole

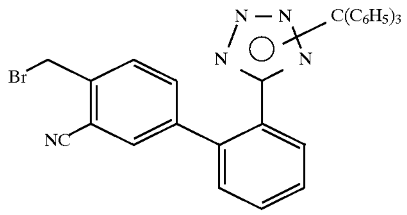

588 mg of the title compound are obtained from 577 mg (2.2 mmol) of the compound of Example XLII analogously to the instructions of Example XXXVI.

Yield: 50.5% of theory

Melting point: 194° C.

EXAMPLE XLIV

4-Formyl-3-methoxyphenyl trifluoromethanesulphonate

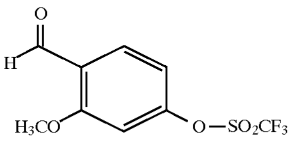

The title compound is obtained from 15.2 g (0.1 mol) of 2-methoxy-4-hydroxy-benzaldehyde and 31 g (0.11 mol) of trifluoromethanesulphonic anhydride analogously to the instructions of Example XXXIII.

Yield: 15.8 g (59% of theory)

$R_f$: 0.38 (petroleum ether/ethyl acetate=20:1)

EXAMPLE XLV

2-Methoxy-4-methylphenyl trifluoromethanesulphonate

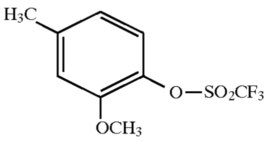

The title compound is obtained from 13.8 g (0.1 mol) of 2-methoxy-4-methylphenol and 31 g (0.11 mol) of trifluoromethanesulphonic anhydride analogously to the instructions of Example XXXIII.

Yield: 26.5 g (98% of theory)

$R_f$: 0.76 (petroleum ether/ethyl acetate=3:1)

EXAMPLE XLVI

N-Triphenylmethyl-5-[2-(4'-formyl-3'-methoxybiphenyl)]tetrazole

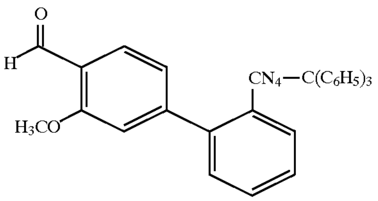

The title compound is obtained from 2.46 g (10 mmol) of the compound from Example XLIV analogously to the instructions of Example XXXIV.

Yield: 3.1 g (56% of theory)

$R_f$: 0.44 (petroleum ether/ethyl acetate=5:1)

EXAMPLE XLVII

N-Triphenylmethyl-5-[2-(2'-methoxy-4'-methylbiphenyl)]tetrazole

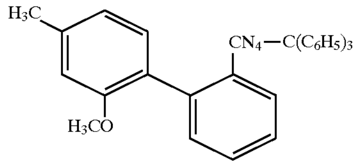

The title compound is obtained from 2.0 g (7.4 mmol) of the compound from Example XLV analogously to the instructions of Example XXXIV.

Yield: 1.75 g (47% of theory)

$R_f$: 0.48 (petroleum ether/ethyl acetate=5:1)

EXAMPLE XLVIII

N-Triphenyl-5-[2-(4'-hydroxymethyl-3'-methoxybiphenyl)]tetrazole

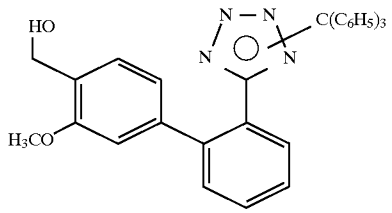

A solution of 15.9 g (30.5 mmol) of the compound from Example XLVI in 450 ml of dry tetrahydrofuran is added dropwise to 9.14 ml (9.14 mmol) of a 1M solution of lithium aluminium hydride in tetrahydrofuran at 0° C. under argon. The cooling bath is then removed, the mixture is stirred at 20° C. for 30 minutes, 50 ml of water and 30 ml of 15% strength sodium hydroxide solution are added and the solvent is removed in vacuo. The residue is taken up in methylene chloride/water and the aqueous phase is extracted twice with methylene chloride. The combined organic phases are washed twice with saturated sodium chloride solution, dried over sodium sulphate and concentrated. The residue is purified on silica gel using petroleum ether/ethyl acetate (10:1, 5:1, 3:1, 1:1).

Yield: 11.5 g (72% of theory)

$R_f$: 0.2 (petroleum ether/ethyl acetate=3:1)

EXAMPLE XLIX

N-Triphenylmethyl-5-[2-(4'-bromomethyl-3'-methoxybiphenyl)]tetrazole

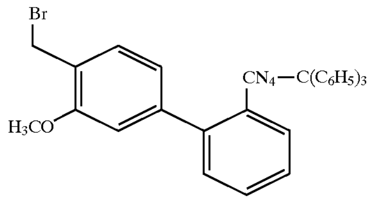

6.2 g (23 mmol) of phosphorus tribromide are added dropwise to a solution of 11.5 g (21.8 mmol) of the compound from Example XLVIII in 42 ml of ether at 0° C. and the mixture is stirred at 0° C. for 1 hour. The reaction mixture is poured onto ice-water and extracted three times with ethyl acetate and the combined organic phases are washed twice with saturated sodium bicarbonate solution, dried over sodium sulphate and concentrated. The residue is reacted further without purification.

Yield: 8 g (crude, 62% of theory)

$R_f$: 0.56 (petroleum ether/ethyl acetate=5:1)

EXAMPLE L

N-Triphenylmethyl-5-[2-(4'-bromomethyl-2'-methoxybiphenyl)]tetrazole

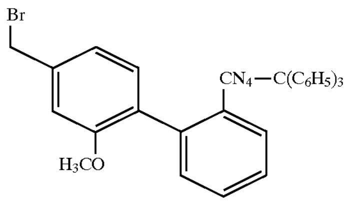

The title compound is obtained from 7.73 g (15.2 mmol) of the compound from Example XLVII analogously to the instructions of Example VII.

Yield: 6.57 g (74% of theory)

$R_f$: 0.41 (petroleum ether/ethyl acetate=10:1)

EXAMPLE LI

6-Butyl-4-methoxycarbonyl-2-oxo-1-{[2-chloro-2' (N-triphenylmethyl-tetrazol-5-yl)-biphenyl-4-yl]-methyl}-1,2-dihydropyridine

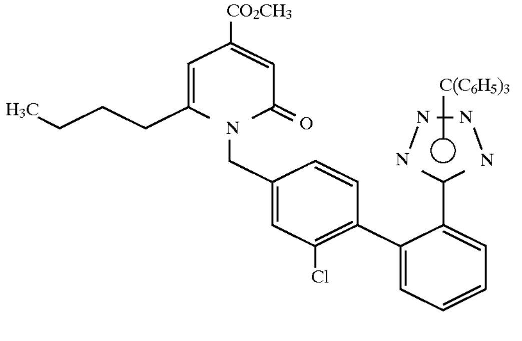

6.60 g of the title compound [34.6% of theory, $R_f$ 0.35 (hexane:ethyl acetate=3:1)] are obtained from 6.11 g (29.2 mmol) of the compound from Example VIII and 15.7 g (26.5 mmol) of the compound from Example XXXVI analogously to Example IX.

The compounds listed in Table II are prepared analogously to the instructions of Example IX:

TABLE II

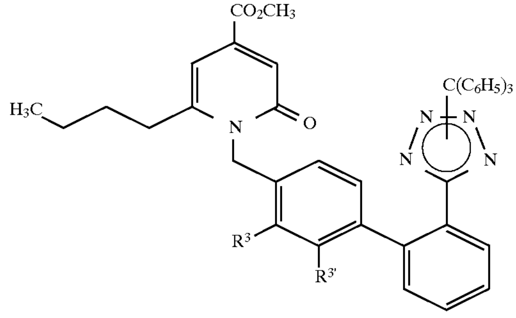

| Ex. No. | $R^3$ | $R^{3'}$ | $R_f$ |
|---|---|---|---|
| LII | H | CN | 0.35 cyclohexene:ethyl acetate 10:1 |
| LIII | $OCH_3$ | H | 0.46 petroleum ether/ethyl acetate 1:1 |
| LIV | H | $OCH_3$ | 0.39 petroleum ether/ethyl acetate 1:1 |

EXAMPLE LV

6-Butyl-4-methoxycarbonyl-2-oxo-1-{[3-chloro-2'-(N-triphenylmethyl-tetrazol-5-yl)-biphenyl-4-yl] methyl}-1,2-dihydropyridine

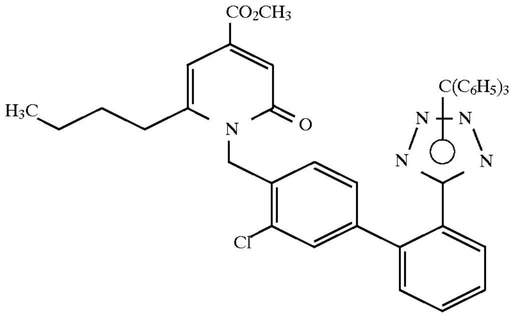

Argon is passed through a suspension of 5.3 g (12 mmol) of the compound from Example XXIII, 5.0 g (12 mmol) of 2-(N-triphenylmethyl-tetrazol-5-yl)-phenylboronic acid and 1.22 g (11.5 mmol) of sodium carbonate in 14 ml of water, 14 ml of methanol and 110 ml of toluene, and 0.70 g (0.61 mmol) of tetrakistriphenyl-phosphinepalladium(0) is then added. The reaction mixture is heated at 90° C. overnight, diluted with water at room temperature and extracted with ethyl acetate. Washing of the organic phase is carried out with saturated sodium chloride solution, and drying is carried out over sodium sulphate. Concentration and chromatography over silica gel (ethyl acetate:petroleum ether=1:3) give 3.44 g of the title compound (41% of theory; $R_f$ 0.23 (ethyl acetate:petroleum ether=1:3).

The examples listed in Table III are prepared analogously to the instructions of LV:

TABLE III

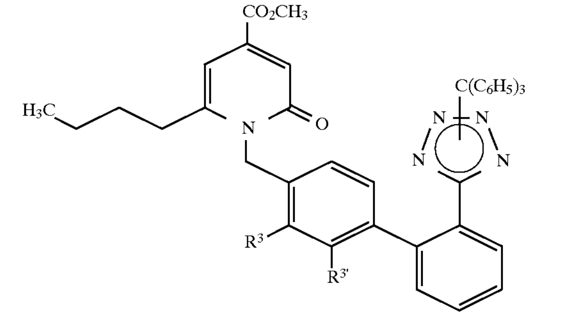

| Ex. No. | $R^{3'}$ | $R^3$ | $R_f$ |
|---|---|---|---|
| LVI | $NO_2$ | H | 0.12 (hexane:ethyl acetate = 3:1) |
| LVII | H | $NO_2$ | 0.27 (hexane:ethyl acetate = 2:1) |
| LVIII | H | $CH_3$ | 0.63 (toluene:ethyl acetate: glacial acetic acid 20:20:1) |

PREPARATION EXAMPLES

Example 1

6-Butyl-4-methoxycarbonyl-2-oxo-1-[(3-fluoro-2'-tetrazol-5-yl-biphenyl-4-yl)-methyl]-1,2-dihydropyridine

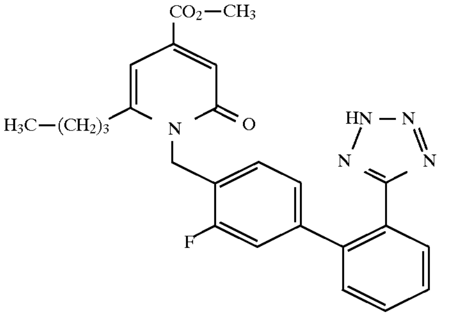

A solution of 3.0 g (4.2 mmol) of the compound from Example IX in 40 ml of acetone is stirred with 0.4 ml of 37% strength hydrochloric acid at room temperature for 30 minutes and then heated on a water-bath for about 1 minute. After addition of a further 0.4 mol of 37% strength hydrochloric acid, the process is repeated. The mixture is concentrated to dryness and the residue is chromatographed on 90 g of silica gel (230–400 mesh using methylene chloride:methanol 50:1→20:1).

Yield: 1,6 g (81% of theory)

$R_f$=0.49 (toluene:ethyl acetate:glacial acetic acid 10:30:1)

Example 2

6-Butyl-4-methoxycarbonyl-2-oxo-1-{[3-methoxy-2'-(tetrazol-5-yl)-biphenyl-4-yl]-methyl}-1,2-dihydropyridine

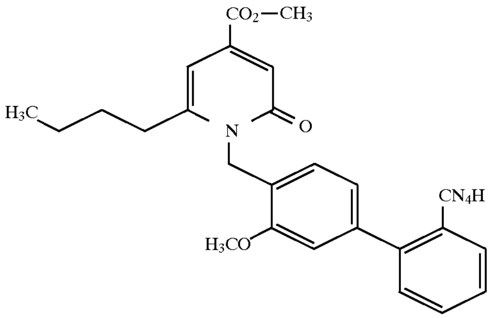

The title compound is obtained from 435 mg (0.61 mmol) of the compound from Example LIII analogously to the instructions of Example 1.

Yield: 162 mg (56% of theory)

$R_f$: 0.33 (toluene/ethyl acetate/glacial acetic acid=20:20:1)

Example 3

6-Butyl-4-methoxycarbonyl-2-oxo-1-{[2-methoxy-2'-(tetrazol-5-yl)-biphenyl-4-yl]-methyl}-1,2-dihydropyridine

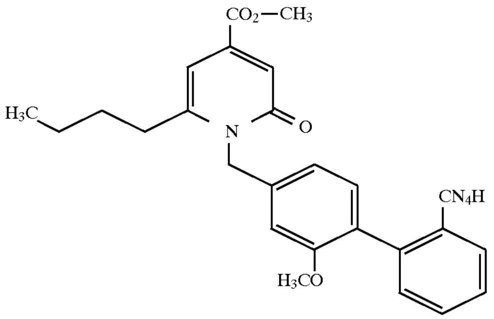

The title compound is obtained from 740 mg (1.03 mmol) of the compound from Example LIV analogously to the instructions of Example 1.

Yield: 455 mg (93% of theory)

$R_f$: 0.28 (toluene/ethyl acetate/glacial acetic acid=20:20:1)

Example 4

6-Butyl-4-methoxycarbonyl-2-oxo-1-{[2-methyl-2'-(tetrazol-5-yl)-biphenyl-4-yl]-methyl}-1,2-dihydropyridine

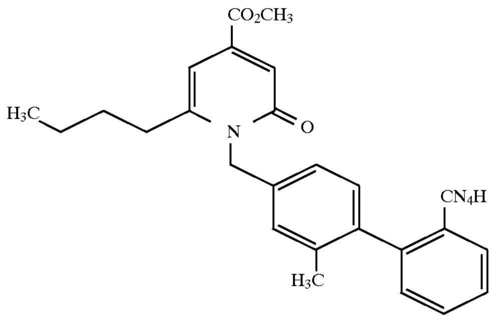

The title compound is obtained from 1.0 g (1.42 mmol) of the compound from Example LVIII analogously to the instructions of Example 1.

Yield: 513 mg (79% of theory)

$R_f$: 0.11 (toluene/ethyl acetate/glacial acetic acid=30:20:1)

Example 5

6-Butyl-4-methoxycarbonyl-2-oxo-1-{[2-cyano -2'-(tetrazol-5-yl)-biphenyl-4-yl]-methyl}-1,2-dihydropyridine

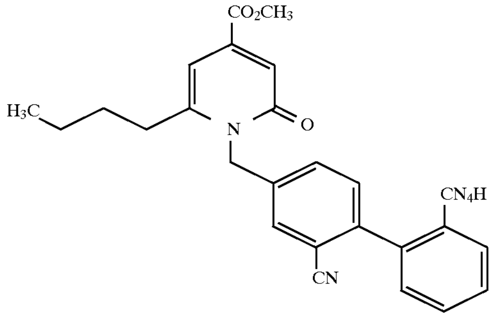

The title compound is obtained from 1.0 g (1.13 mmol) of the compound from Example LII analogously to the instructions of Example 1.

Yield: 679 mg (91.1 % of theory)

Melting point: 210°–215° C. (decomposition)

Example 6

6-Butyl-4-methoxycarbonyl-2-oxo-1-{[3-chloro-2'-(tetrazol-5-yl)-biphenyl-4-yl]-methyl}-1,2-dihydropyridine

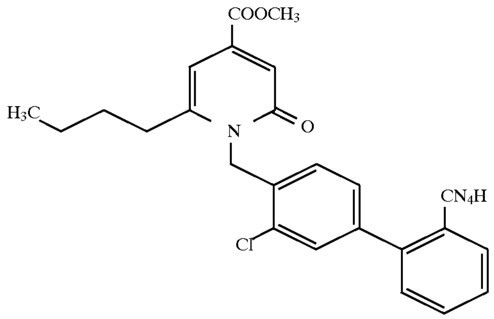

The title compound is obtained from 3.4 g (4.7 mmol) of the compound of Example LV analogously to the instructions of Example 1.

Yield: 1.7 g (75% of theory)

$R_f$: 0.25 (methylene chloride:methanol 10:1)

Example 7

6-Butyl-4-methoxycarbonyl-2-oxo-1-{[2-chloro-2'-(tetrazol-5-yl)-biphenyl-4-yl]-methyl}-1,2-dihydropyridine

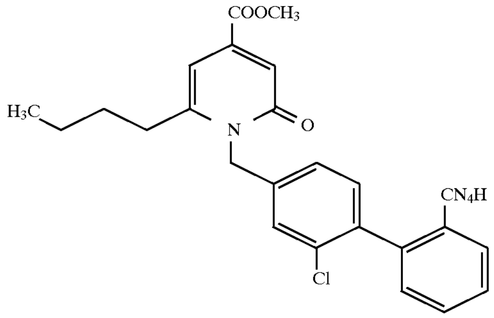

The title compound is obtained from 394 mg (0.55 mmol) of the compound of Example LI analogously to the instructions of Example 1.

Yield: 115 mg (44% of theory)

$R_f$: 0.29 (methylene chloride:methanol 20:1)

Example 8

6-Butyl-4-methoxycarbonyl-2-oxo-1-{[3-nitro-2'-(tetrazol-5-yl)-biphenyl-4-yl]-methyl}-1,2-dihydropyridine

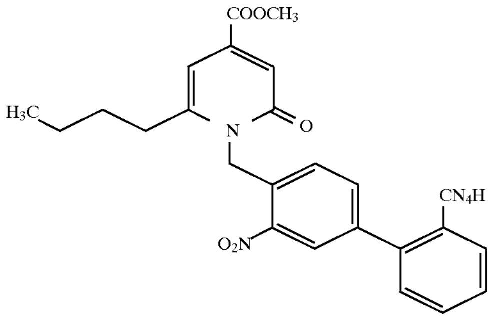

The title compound is obtained from 390 mg (0.53 mmol) of the compound of Example LVI analogously to the instructions of Example 1.

Yield: 135 mg (52% of theory)

$R_f$: 0.28 (methylene chloride:methanol 10:1)

Example 9

6-Butyl-4-methoxycarbonyl-2-oxo-1-{[2-nitro-2'-(tetrazol-5-yl)-biphenyl-4-yl]-methyl}-1,2-dihydropyridine

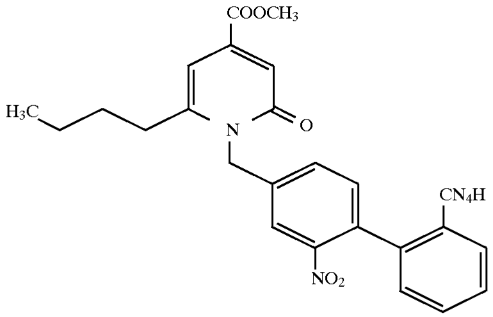

The title compound is obtained from 790 mg (1.1 mmol) of the compound of Example LVII analogously to the instructions of Example 1.

Yield: 296 mg (56% of theory)

$R_f$: 0.29 (methylene chloride:methanol 10:1)

The compounds listed in the following Table 1 are prepared analogously to Example 1:

TABLE 1

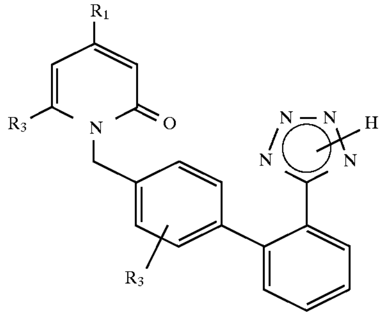

| Ex. No. | $R_1$ | $R_2$ | $R_3$ | Salt/acid |
|---|---|---|---|---|
| 10 | $CO_2H$ | $C_4H_9$ | 3-F | acid |
| 11 | $CO_2H$ | $C_4H_9$ | 2-Cl | acid |
| 12 | $CO_2H$ | $C_4H_9$ | 3-Cl | acid |
| 13 | $CO_2C_2H_5$ | $C_4H_9$ | 2-Me | acid |
| 14 | $CO_2CH_3$ | $C_3H_7$ | 3-Me | mono-Li salt |
| 15 | $CO_2H$ | $C_4H_9$ | 2-OH | acid |
| 16 | $CO_2C_2H_5$ | $C_4H_9$ | 3-OH | acid |
| 17 | $CO_2H$ | $C_4H_9$ | 2-$CF_3$ | di-Na salt |
| 18 | $CO_2H$ | $C_3H_7$ | 3-$CF_3$ | acid |
| 19 | $CO_2CH_3$ | $C_3H_7$ | 2-$OCF_3$ | acid |
| 20 | $CO_2H$ | $C_4H_9$ | 3-$OCF_3$ | di-Na salt |
| 21 | $CO_2CH_3$ | $C_4H_9$ | 2-F | acid |
| 22 | $CO_2CH_3$ | $C_4H_9$ | 2-F | mono-K salt |
| 23 | $CO_2H$ | $C_4H_9$ | 2-F | acid |
| 24 | $CO_2CH_3$ | $C_4H_9$ | 2-Cl | mono-K salt |
| 25 | $CO_2CH_3$ | $C_4H_9$ | 3-F | mono-K salt |
| 26 | $CO_2CH_3$ | $C_4H_9$ | 3-Cl | mono-K salt |
| 27 | $CO_2CH_3$ | $C_5H_{11}$ | 3-F | acid |

Example 28

6-Butyl-4-carboxy-2-oxo-1-[(3'-fluoro-2'-tetrazol-5-yl-biphenyl-4-yl)-methyl]-1,2-dihydropyridine

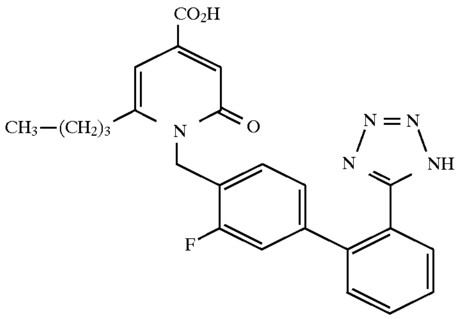

260 mg (10 mol %) of tetrakistriphenylphosphinepalladium(0), 6.75 ml (13.5 mmol) of 2M sodium carbonate solution, 513 mg (2.7 mmol) of the compound of Example X and 1.5 ml of ethanol are added successively to a solution of 1 g (2.25 mmol) of the compound from Example XVIII in 20 ml of DME and the mixture is heated under reflux for 16 hours. After cooling, the reaction mixture is filtered over kieselguhr with suction and subsequently rinsed with methanol, the solvent is removed and the residue is purified on silica gel using toluene/ethyl acetate/glacial acetic acid (35:5:1 and 30:10:1).

Yield: 219 mg (22% of theory)

$R_f$: 0.16 (toluene/ethyl acetate/glacial acetic acid=10:30:1)

The compounds listed in Table 2 are prepared analogously to the instructions of Example 28:

TABLE 2

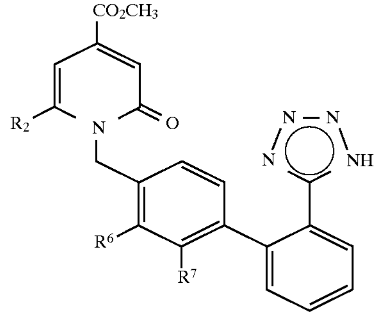

| Ex. No. | $R_2$ | $R_6$ | $R_6$ | $[M + H]^+$ | $R_f$ |
|---|---|---|---|---|---|
| 29 | $CH_3-(CH_2)_3-$ | $-CN$ | H | | |
| 30 | $CH_3-(CH_2)_3-$ | $-CH_3$ | H | | 0.24 (A) |
| 31 | $CH_3-(CH_2)_3-$ | H | F | | 0.22 (B) |
| 32 | $CH_3-(CH_2)_4-$ | F | H | 462 | 0.66 (A) |

A: toluene/ethyl acetate/glacial acetic acid = 10:30:1
B: methylene chloride/methanol/glacial acetic acid = 10:1:0.3

TABLE 3

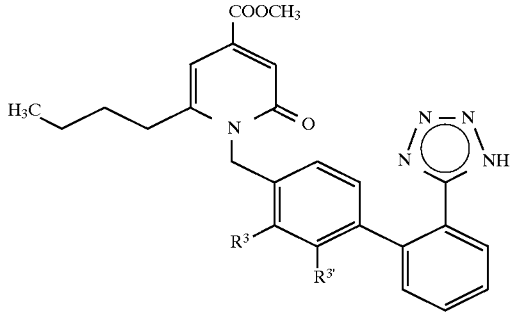

| Ex. No. | $R_3$ | $R_3$ | $R_f$ |
|---|---|---|---|
| 34 | H | F | 0.40 methylene chloride:methanol 10:1 |
| 35 | $COOCH_3$ | H | 0.50 methylene chloride:methanol: glacial acetic acid 100:10:3 |
| 36 | CN | H | 0.38 methylene chloride:methanol 5:1 |
| 37 | F | H | 0.49 toluene:ethyl acetate:glacial acetic acid = 10:30:1 |
| 38 | $CH_3$ | H | 0.49 toluene:ethyl acetate:glacial acetic acid 20:20:1 |

Example 33

6-Butyl-4-methoxycarbonyl-2-oxo-1-[(2-methoxycarbonyl-2'-tetrazol-5-yl-biphenyl-4-yl)-methyl]-1,2-dihydropyridine

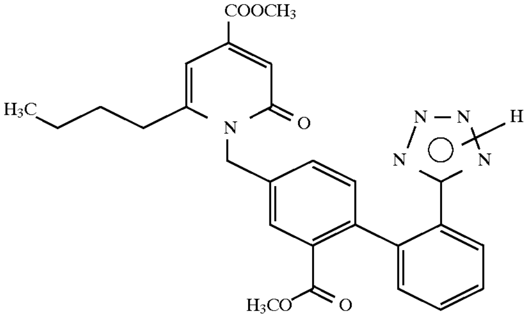

204 ml of thionyl chloride are added to a solution of 166 mg (0.35 mmol) of the compound from Example 50 in 5 ml of methanol and the mixture is heated under reflux for 3 hours. It is concentrated to dryness and the residue is chromatographed over silica gel using methylene chloride:methanol (20:1) to give 131 mg of the title compound.

Yield: 74.6% of theory $R_f$: 0.54 (methylene chloride:methanol 5:1)

The compounds listed in Table 3 were prepared analogously to the instructions of Example 33:

Example 39

6-Butyl-4-methoxycarbonyl-2-oxo-1-[(2-aminocarbonyl-2'-tetrazol-5-yl-biphenyl-4-yl)-methyl]-1,2-dihydropyridine potassium salt

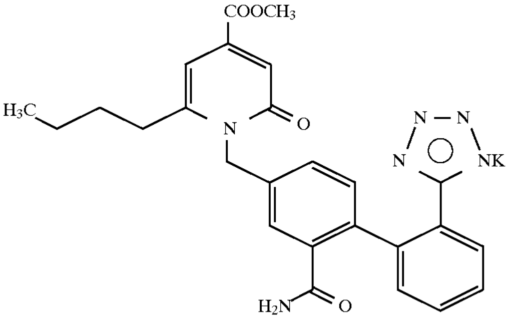

A solution of 400 mg (0.82 mmol) of the compound from Example 48 is stirred with 1644 ml (0.82 mmol) of a 0.5N potassium bicarbonate solution. The mixture is diluted with 10 ml of water, the tetrahydrofuran is distilled off in vacuo and the aqueous product solution is freeze-dried to give 399 mg of the title compound.

Yield: 92.5% of theory

MS(FAB) 487 (M+H) 525 (M+K+H)

The compounds listed in Table 4 are prepared analogously to the instructions of Example 39:

TABLE 4

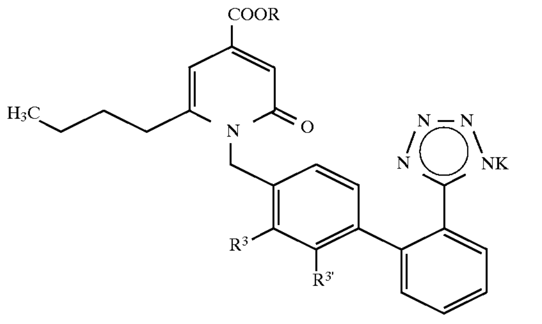

| Ex. No. | $R^3$ | $R^{3'}$ | R |
|---|---|---|---|
| 40 | H | CN | $CH_3$ |
| 41 | H | CN | K |
| 42 | H | F | K |
| 43 | H | F | $CH_3$ |
| 44 | CN | H | $CH_3$ |
| 45 | CN | H | K |
| 46 | F | H | $CH_3$ |
| 47 | F | H | K |

Example 48

6-Butyl-4-methoxycarbonyl-2-oxo-1-[(2-aminocarbonyl-2'-tetrazol-5-yl-biphenyl-4-yl)-methyl]-1,2-dihydropyridine

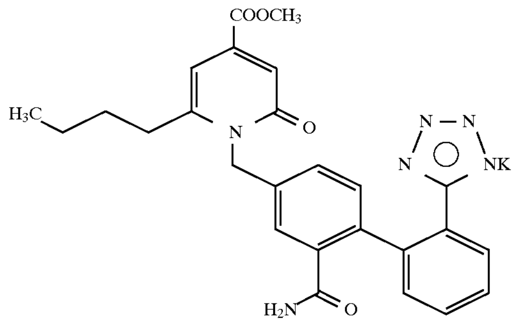

A suspension of 708 mg (1.5 mmol) of the compound from Example 5 in 20 ml of methanol is saturated with hydrogen chloride gas, and the resulting clear solution is stirred at 20° C. for 48 hours. It is concentrated to dryness and the residue is chromatographed on silica gel using ethyl acetate:methanol:water mixtures of 20:1:0→100:15:5 to give 586 mg of the title compound.

Yield: 79.7% of theory $R_f$=0.2 (ethyl acetate:methanol:water 100:15:5)

Example 49

6-Butyl-4-carboxy-2-oxo-1-[(2-aminocarbonyl-2'-tetrazol-5-yl-biphenyl-4-yl)-methyl]-1,2-dihydropyridine dipotassium salt

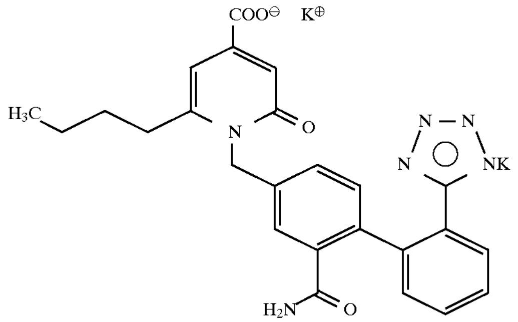

A solution of 100 mg (0.2 mmol) of the compound from Example 48 in 7 ml of tetrahydrofuran and 421 ml (0.421 mmol) of a 1N potassium hydroxide solution are stirred at 20° C. for 4 hours and then diluted with 10 ml of water, the tetrahydrofuran is distilled off in vacuo and the aqueous solution is freeze-dried to give 103 mg of the title compound.

Yield: 91.1% of theory $R_f$: 0.15 (methylene chloride:methanol:acetic acid 100:10:3)

Example 50

6-Butyl-4-carboxy-2-oxo-1-[(2-carboxy-2'-tetrazol-5-yl-biphenyl-4-yl)-methyl]-1,2-dihydropyridine

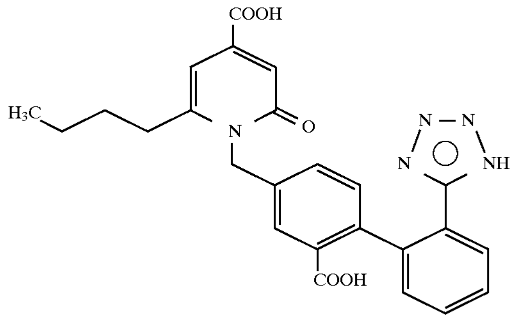

A solution of 708 mg (1.5 mmol) of the compound from Example 40 in 3 ml of 5N sodium hydroxide solution is stirred under reflux for 2 hours, diluted with 200 ml of water and 10 ml of ethyl acetate at 20° C. and brought to pH 1 with hydrochloric acid. The organic phase is separated off and the aqueous phase is dried over sodium sulphate and concentrated, and the residue is chromatographed on silica gel using methylene chloride:methanol:acetic acid mixtures of 100:5:0.5→100:15:5 to give 204 mg of the title compound.

Yield: 37.4% of theory $R_f$: 0.10 (methylene chloride:methanol:acetic acid=100:10:5)

Example 51

6-Butyl-4-carboxy-2-oxo-1-[(2-aminocarbonyl-2'-tetrazol-5-yl-biphenyl-4-yl)-methyl]-1,2-dihydropyridine

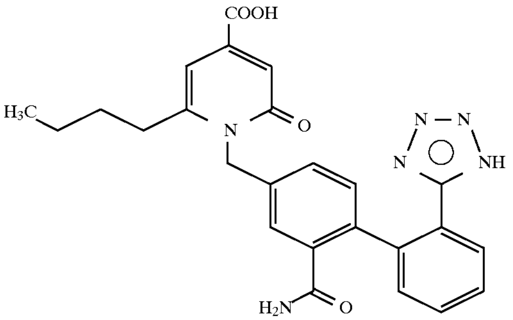

is eluted.

Example 52

6-Butyl-4-carboxy-2-oxo-1-{[3-methoxy-2'-(tetrazol-5-yl)-biphenyl-4-yl]-methyl}-1,2-dihydropyridine

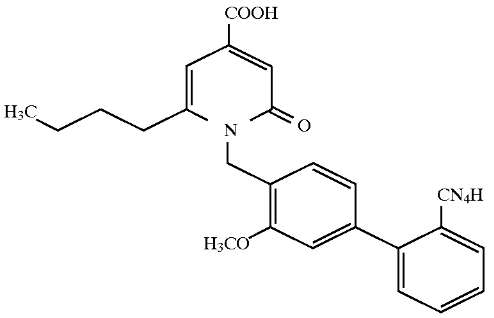

The title compound is obtained from 135 mg (0.28 mmol) of the compound from Example 2 analogously to the instructions of Example 50.

Yield: 59 mg (45% of theory)

$R_f$: 0.17 (toluene/ethyl acetate/glacial acetic acid=20:20:1)

Example 53

6-Butyl-4-carboxy-2-oxo-1-{[2-methoxy-2'-(tetrazol-5-yl)-biphenyl-4-yl]-methyl}-1,2-dihydropyridine

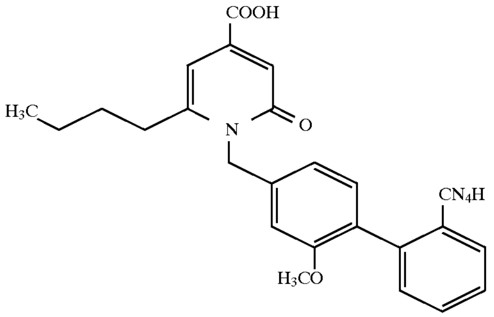

The title compound is obtained from 393 mg (0.83 mmol) of the compound from Example 3 analogously to the instructions of Example 50.

Yield: 363 mg (95% of theory)

$R_f$: 0.11 (toluene/ethyl acetate/glacial acetic acid=10:30:1)

Example 54

6-Butyl-4-carboxy-2-oxo-{[3-methyl-2'-(tetrazol-5-yl)-biphenyl-4-yl]-methyl}-1,2-dihydropyridine

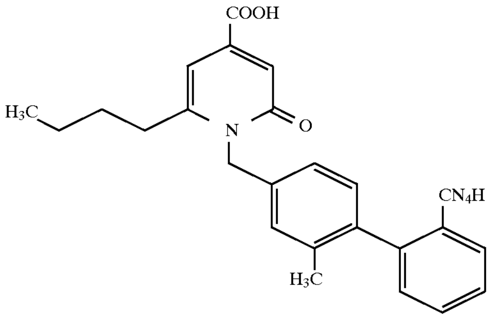

The title compound is obtained from 475 mg (1.04 mmol) of the compound from Example 4 analogously to the instructions of Example 50.

Yield: 386 mg (84% of theory)

$R_f$: 0.17 (toluene/ethyl acetate/glacial acetic acid=10:30:1)

Example 55

6-Butyl-4-carboxy-2-oxo-1-{[2-cyano-2'-(tetrazol-5-yl)-biphenyl-4-yl]-methyl}-1,2-dihydropyridine

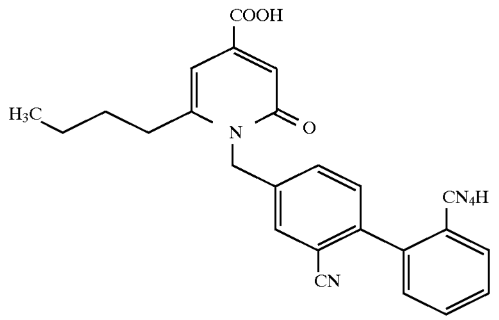

The title compound is obtained from 234 mg (0.5 mmol) of the compound from Example 5 analogously to the instructions of Example 50.

Yield: 221 mg (97.2% of theory)

$R_f$: 0.22 (methylene chloride:methanol:glacial acetic acid 100:10:3)

Example 56

6-Butyl-4-carboxy-2-oxo-1-{[3-carboxymethyl-2'-(tetrazol-5-yl)-biphenyl-4-yl]-methyl}-1,2-dihydropyridine

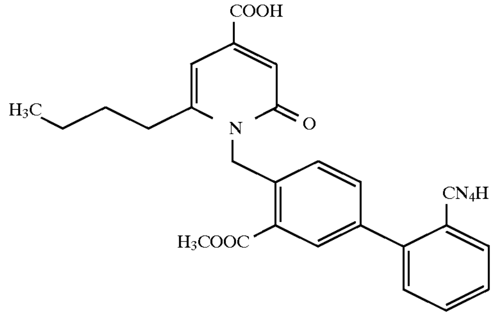

The title compound is obtained from 89 mg (0.18 mmol) of the compound from Example 35 analogously to the instructions of Example 50.

Yield: 57 mg (66% of theory)

$R_f$: 0.26 (methylene chloride:methanol:glacial acetic acid 100:10:3)

Example 57

6-Butyl-4-carboxy-2-oxo-1-{[3-cyano-2'-(tetrazol-5-yl)-biphenyl-4-yl]-methyl}-1,2-dihydropyridine

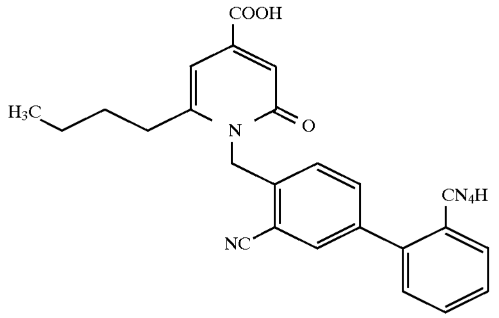

The title compound is obtained from 1.5 mg (3.2 mmol) of the compound from Example 36 analogously to the instructions of Example 50.

Yield: 1.4 mg (100% of theory)

$R_f$: 0.23 (methylene chloride:methanol:glacial acetic acid 100:10:3)

Example 58

6-Butyl-4-carboxy-2-oxo-1-{[3-aminocarbonyl-2'-(tetrazol-5-yl)-biphenyl-4-yl]-methyl}-1,2-dihydropyridine disodium salt

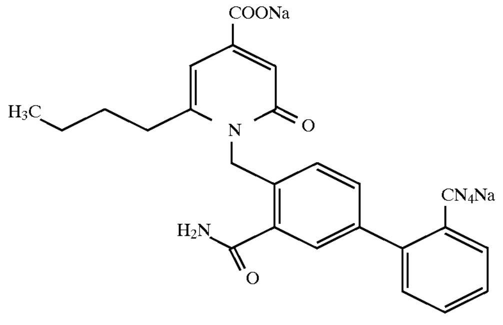

A solution of 134 mg (0.28 mmol) of the compound from Example 59 and 541 μl (0.54 mmol) of a 1N sodium hydroxide solution in 4 ml of tetrahydrofuran is stirred at 20° C. for 1 hour, diluted with 10 ml of water and concentrated and the aqueous solution which remains is freeze-dried.

Yield: 142 mg (99.6% of theory)

MS(FAB) 495 (M+Na), 517 (M+2 $Na^{-}H$) 539 (M+3 Na −2H)

Example 59

6-Butyl-4-methoxycarbonyl-2-oxo-1-{[3-aminocarbanyl-2'-(tetrazol-5-yl)-biphenyl-4-yl]-methyl}-1,2-dihydropyridine

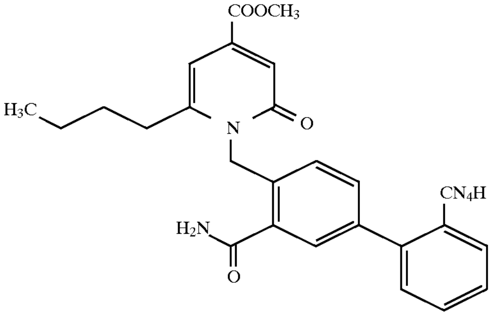

A solution of 937 mg (2 mmol) of the compound from Example 36 in 20 ml of methanol is saturated with hydrogen chloride gas and stirred at 20° C. for 48 hours. The mixture is concentrated to dryness, the residue is taken up in 100 ml of water, the mixture is washed three times with 30 ml of ethyl acetate each time and the combined organic phases are washed three times with 30 ml of sodium bicarbonate solution each time. The aqueous phases are brought to pH 1 and washed three times with 30 ml of ethyl acetate each time, the combined organic phases are dried over sodium sulphate and concentrated and the residue is chromatographed on silica gel using ethyl acetate/methanol/water mixtures (20:1:0→100:20:8) to give 472 mg of the title compound.

Yield: 47% of theory $R_f$: 0.55 (methylene chloride:methanol:glacial acetic acid 100: 10:3)

Example 60

6-Butyl-4-carboxy-2-oxo-1-{[3-carboxy-2'-(tetrazol-5-yl)-biphenyl-4-yl]-methyl}-1,2-dihydropyridine

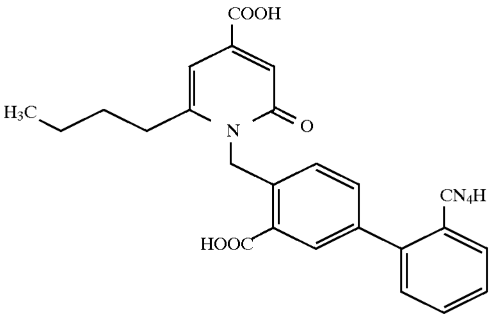

A solution of 937 mg (2 mmol) of the compound from Example 36 in 4 ml of a 5N sodium hydroxide solution is heated under reflux for 3 hours, diluted with 30 ml of water and 10 ml of ethyl acetate at 20° C., brought to pH 1 and washed three times with 10 ml of ethyl acetate each time, the combined organic phases are dried over sodium sulphate and concentrated and the residue is chromatographed on silica gel using methylene chloride:methanol:glacial acetic acid mixtures 100:6:1→100:15:5 to give 425 mg of the title compound.

Yield: 44.9% of theory $R_f$: 0.11 (methylene chloride:methanol:glacial acetic acid 100:10:3)

We claim:

1. A method of treating atherosclerosis in a patient in need thereof which comprises administering to said patient an effective amount therefor of a compound of the formula:

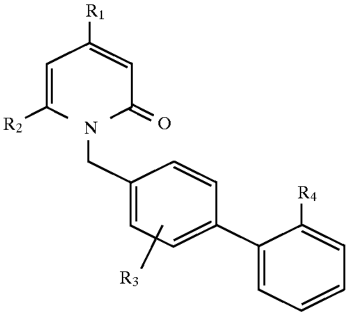

wherein $R_1$ represents a carboxyl group or a $C_{1-8}$-alkoxycarbonyl group;

$R_2$ represents straight-chain or branched $C_{1-8}$-alkyl;

$R_3$ represents halogen; and $R_4$ represents a carboxyl group or a tetrazolyl group;

or a salt of said compound.

2. The method according to claim 1, wherein the compound is 6-butyl-4-methoxycarbonyl-2-oxo-1-[3-fluoro-2'-tetrazol-5-yl-biphenyl-4-yl)methyl]-1,2-dihydropyridine of the formula

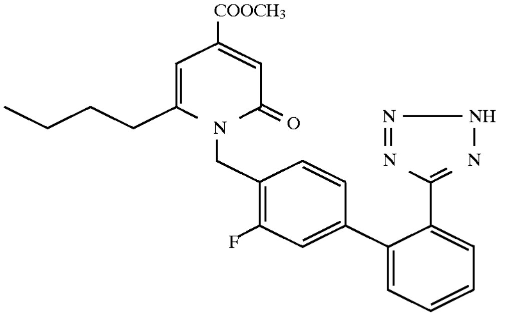

or a salt thereof.

3. The method according to claim 1, wherein the compound is 6-butyl-4-methoxycarbonyl-2-oco-1-[(3-chloro-2'-tetrazol-5-yl-biphenyl-4-yl)methyl]-1,2-dihydropyridine of the formula

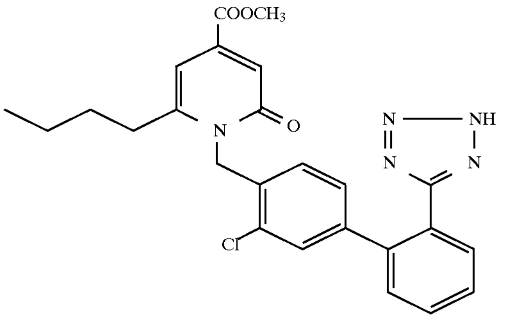

or a salt thereof.

4. The method according to claim 1, wherein the compound is 6-butyl-4-carboxyl-2-oxo-1-[(3-fluoro-2'-tetrazol- 5-yl-biphenyl-4-yl)methyl]-1,2-dihydropyridine of the formula

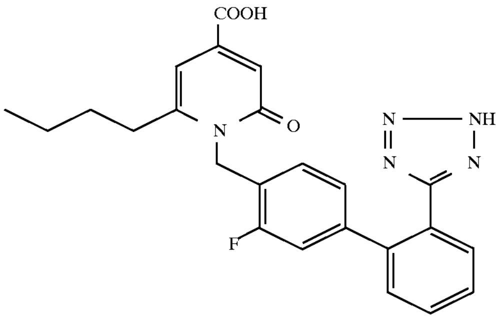

or a salt thereof.

5. A process for preparing a trisubstituted biphenyl compound of the formula (I)

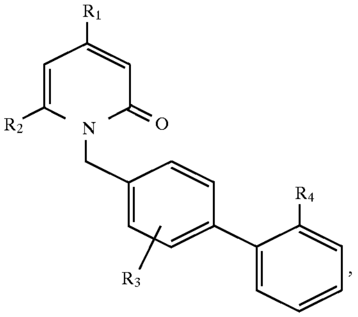

in which $R_1$ represents a carboxyl radical; or represents a $C_1$–$C_8$-alkoxycarbonyl radical;

$R_2$ represents straight-chain or branched $C_1$–$C_8$-alkyl;

$R_3$ represents halogen, hydroxyl, cyano, $C_1$–$C_6$-alkoxy, straight-chain or branched $C_1$–$C_8$-alkyl, trifluoromethyl, trifluoromethoxy, carboxamido, carboxyl, $C_1$–$C_8$-alkoxycarbonyl or nitro; and $R_4$ represents tetrazolyl;

or a salt thereof;

said process comprising reacting a compound of the formula (IV):

(IV)

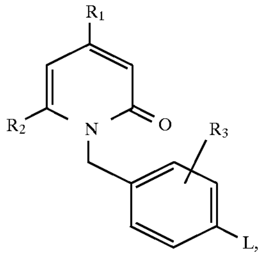

in which

L represents a leaving group; with a compound of the formula (V):

(V)

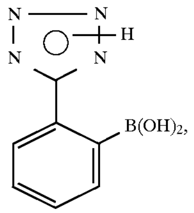

in an inert solvent, in the presence of a base and a metal catalyst or a phase transfer catalyst.

6. The process according to claim 5, wherein L represents a leaving group selected from the group consisting of bromine, iodine and methane-, toluene-, fluorine- and trifluoromethane sulphonyloxy.

7. The process according to claim 5, wherein said reaction results in a compound of formula (I) wherein $R_1$ is a $C_{1-8}$-alkoxycarbonyl radical, which subsequently is converted to a carboxyl radical by hydrolysis of the $C_{1-8}$-alkoxycarbonyl radical.

8. The process according to claim 5, wherein the solvent is selected from the group consisting of ethers, hydrocarbons, halogenohydrocarbons, and mixtures thereof with each other and/or with water.

9. The process according to claim 5, wherein the solvent is selected from the group consisting of diethyl ether, dioxane, tetrahydrofuran, dimethoxyethane, benzene, toluene, xylene, hexane, cyclohexane, petroleum fractions, methylene chloride, chloroform, carbon tetrachloride, dichloroethylene, trichloroethylene, chlorobenzene, ethyl acetate, triethylamine, pyridine, dimethyl sulphoxide, dimethylformamide, hexamethylphosphoric acid triamide, acetonitrile, acetone, nitromethane, and mixtures thereof with each other and/or with water.

10. The process according to claim 5, wherein the base is selected from the group consisting of organic tertiary, non-nucleophilic bases and inorganic bases.

11. The process according to claim 5, wherein the base is selected from the group consisting of triethylamine, diisopropylethylamine, potassium carbonate or hydroxide, sodium carbonate or hydroxide, thallium carbonate or hydroxide, or alkoxides of potassium, sodium or thallium.

12. The process according to claim 5, wherein a metal catalyst is used and is selected from the group consisting of metal complexes of nickel, palladium and platinum.

13. The process according to claim 5, wherein a metal catalyst is used and the metal catalyst is tetrakistriphenyl phosphine palladium.

14. The process according to claim 5, wherein a phase transfer catalyst is used and the phase transfer catalyst is selected from the group consisting of tetra-n-butylammonium bromide and crown ethers.

15. A process for preparing a compound of the formula:

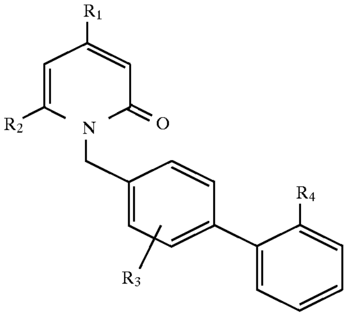

wherein $R_1$ represents a carboxyl group or a $C_{1-8}$-alkoxycarbonyl group;

$R_2$ represents a straight-chain or branched $C_{1-8}$-alkyl;

$R_3$ represents halogen; and $R_4$ represents a tetrazolyl group;

or a salt of said compound;

said process comprising reacting a compound of the formula (IV):

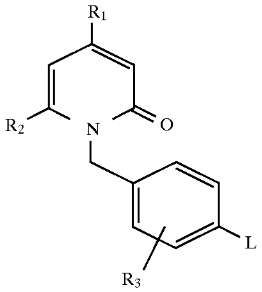

(IV)

in which

L represents a leaving group;

with a compound of the formula (V):

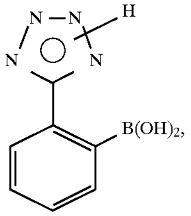

(V)

in an inert solvent, in the presence of a base and a metal catalyst or a phase transfer catalyst.

* * * * *